(12) United States Patent
Adams, Jr. et al.

(10) Patent No.: US 10,092,724 B2
(45) Date of Patent: Oct. 9, 2018

(54) RETENTION DRAINAGE CATHETER

(71) Applicant: Lamina Solutions LLC, Jackson, MS (US)

(72) Inventors: John D. Adams, Jr., Jackson, MS (US); Dean Brent Barron, Jackson, MS (US)

(73) Assignee: LAMINA SOLUTIONS LLC, Jackson, MS (US)

( * ) Notice: Subject to any disclaimer, the term of this patent is extended or adjusted under 35 U.S.C. 154(b) by 652 days.

(21) Appl. No.: 14/546,382

(22) Filed: Nov. 18, 2014

(65) Prior Publication Data

US 2015/0094696 A1  Apr. 2, 2015

Related U.S. Application Data

(63) Continuation-in-part of application No. 14/272,270, filed on May 7, 2014.

(60) Provisional application No. 61/826,869, filed on May 23, 2013, provisional application No. 61/820,532, filed on May 7, 2013.

(51) Int. Cl.
A61M 25/00 (2006.01)
A61M 1/00 (2006.01)
A61M 25/10 (2013.01)

(52) U.S. Cl.
CPC ........ *A61M 25/0017* (2013.01); *A61M 1/008* (2013.01); *A61M 25/1002* (2013.01); *A61M 25/1011* (2013.01); A61M 2025/1093 (2013.01); A61M 2202/0496 (2013.01)

(58) Field of Classification Search
CPC .......... A61M 1/008; A61M 2205/1093; A61M 2202/0496; A61M 25/04; A61M 25/002; A61M 25/1011; A61M 25/0017
See application file for complete search history.

(56) References Cited

U.S. PATENT DOCUMENTS

| 5,049,132 A | 9/1991 | Shaffer et al. |
| 5,308,356 A | 5/1994 | Blackshear, Jr. et al. |
| 5,417,657 A | 5/1995 | Hauer |
| 5,785,641 A | 7/1998 | Davis |
| 6,068,611 A | 5/2000 | Loffler et al. |
| 9,070,717 B2 | 6/2015 | Lee et al. |

(Continued)

FOREIGN PATENT DOCUMENTS

GB  2395436  * 11/2002

*Primary Examiner* — Philip R Wiest
*Assistant Examiner* — Kai Weng
(74) *Attorney, Agent, or Firm* — Bret E. Field; Bozicevic, Field & Francis LLP

(57) ABSTRACT

A multi-lumen catheter, for insertion into and draining a body cavity, that mitigates the risk of obstruction of the drainage ports and drainage lumen of the catheter, reduces the detrimental effects caused by the suction forces of the drainage ports on the body cavity being drained, and reduces the risk of infection of the body cavity being drained by decreasing the residual volume of fluid retained in the body cavity being drained. These advantages are achieved by the novel approach of disposing a perforated filter membrane or a membrane having a relatively large entry port(s) between membrane struts over a segmented retention element and also over the drainage port(s) of the drainage lumen of the catheter thereby creating internal interstitial drainage channels and internal interstitial drainage cavities.

21 Claims, 21 Drawing Sheets

(56) References Cited

U.S. PATENT DOCUMENTS

| | | |
|---|---|---|
| 2002/0032406 A1 | 3/2002 | Kusleika |
| 2009/0088829 A1 | 4/2009 | Wang et al. |
| 2012/0209375 A1 | 8/2012 | Madrid et al. |
| 2012/0289982 A1 | 11/2012 | Gunday et al. |

* cited by examiner

RETENTION DRAINAGE CATHETER

CROSS-REFERENCES TO RELATED APPLICATIONS

This application is a continuation-in-part of U.S. application Ser. No. 14/272,270, filed on May 7, 2014, which claims the benefit of U.S. Provisional Application Nos. 61/820,532, filed May 7, 2013, and 61/826,869, filed May 23, 2013, each of which are incorporated herein by reference in their entirety.

FIELD OF THE INVENTION

The invention relates generally to medical devices and, in particular, to retention drainage catheters.

BACKGROUND OF THE INVENTION

In the medical field, catheters are generally used to drain fluids from a body cavity. In the urology field, a Foley retention drainage catheter, which may be interchangeably referred to as a Foley catheter or drainage catheter, is commonly used to drain a human bladder. There are many medical conditions that necessitate the use of a Foley catheter. The collection of urine and other fluids after a surgical procedure is such a condition. For the past seventy to eighty years the Foley retention drainage catheter, as depicted in FIG. 18 and labeled "PRIOR ART," has been the preferred option to drain and collect urine and other fluids from the bladder. The basic design of a Foley catheter comprises an elongated cylindrical element containing a central drainage lumen running the length of the elongated cylindrical element, having one or more drainage ports in series at or near the distal end, and an expandable retention element, located proximal to the drainage ports, for securing the catheter within the bladder. The retention element is expanded with fluid via an inflation lumen running from the inflation valve located on the proximal end of the elongated cylindrical element to the retention element. The design of the Foley catheter has not undergone significant changes other than changes to the base materials and attempts to give the materials antibacterial properties. Despite its continued use in the health care industry without significant design changes the Foley catheter does have some acknowledged weaknesses.

Firstly, the Foley catheter is susceptible to obstruction of the drainage ports and the drainage lumen of the catheter due to plugging and/or buildup of debris (debris is defined as loose tissue, sediments, clotted blood, redundant bladder mucosa, and any other materials or viscous fluids in the clinical setting). The drainage ports are generally at least twice the cross sectional area of the drainage lumen. This can result in a funneling effect with debris draining into smaller and smaller spaces, thus, resulting in plugs and blockages causing catheter obstruction. Further, due to the drainage ports being in series, if the most proximal drainage port becomes obstructed by debris that extend from the port into the drainage lumen, thus obstructing the drainage lumen, any remaining unobstructed drainage ports are rendered ineffective as they are upstream of the obstruction. Incomplete emptying/drainage of the bladder caused by obstructions in the catheter are significant causes of catheter associated urinary tract infections (UTIs).

Secondly, the drainage ports in the catheter, being limited in number and limited in cumulative cross sectional area as related to the cross sectional area of the drainage lumen, create a suction effect so that when the force of the suction is projected on the bladder mucosa the suction can cause a disruption in the mucosal integrity. This can result in increased risk of pain, bladder spasms, discomfort, and catheter associated UTIs.

Thirdly, yet another problem is the inability of the Foley catheter to completely drain the bladder, even when the drainage system is completely free of obstruction. Due to the aforementioned drainage port locations, when the bladder is actively drained during catheterization, and the bladder wall closes around the retention element, the bladder retains a residual volume of fluid that is not able to reach the drainage ports. This volume of stagnant fluid can contain urine, blood, bacteria, and/or other pathogens that, when not regularly flushed out of the bladder, can set up an infection in the surrounding tissues, form blood clots in the bladder, and/or other conditions detrimental to the patient. It should be understood that catheter associated UTIs are now the most expensive hospital acquired infection according to the Centers for Disease Control and Prevention.

SUMMARY OF THE INVENTION

The aforementioned problems are solved and a technical advance is achieved in an illustrative novel multi-lumen filter membrane internal interstitial drainage channel catheter (also referred to herein as a FMID catheter) for insertion into and draining a body cavity, that mitigates the risk of obstruction of the drainage ports and drainage lumen of the catheter and also reduces the detrimental effects caused by the suction forces of the drainage ports on the body cavity being drained, and reduces the risk of infection of the body cavity being drained by decreasing the residual volume of fluid retained in the body cavity being drained. These advantages and more are achieved by the novel approach of disposing a membrane (which may be perforated) over a retention element (which may be segmented), the proximal drainage ports, and the distal drainage ports of the drainage lumen of the catheter, such that when the retention element is expanded, the membrane creates one or more interstitial spaces or cavities between the membrane and the elongated cylindrical element (catheter tube).

When the retention element and membrane are in their expanded state, expandable cavities (henceforth referred to as internal interstitial drainage cavities) are created between the membrane and the elongated cylindrical element and expand as the membrane is pushed away from elongated cylindrical element. Also, when a segmented retention element and membrane are in their expanded state, other expandable cavities (henceforth referred to as internal interstitial drainage channels) are created between the expanded wedges of the retention element and the membrane in some embodiments. Alternatively, the interstitial drainage channels can be disposed on a segmented retention element such that they are not under the membrane when in the expanded state. The internal interstitial drainage channels are disposed from the distal end of the segmented retention element to the proximal end of the segmented retention element and expand proportionally as the expanded state of the segmented retention element and the membrane is reached. The drainage ports communicate with the internal interstitial drainage cavities. The internal interstitial drainage cavities communicate with the internal interstitial drainage channels. The internal interstitial drainage cavities and/or the internal interstitial drainage channels communicate with the body cavity being drained through the membrane.

The membrane, in the expanded state, provides entry port(s) for fluid to enter into the interstitial drainage cavities and then through the drainage ports of the FMID catheter. One or more entry ports may be larger than the cross sectional area of the drainage ports and the drainage lumen. While the relatively larger entry port size may allow for debris (clots, tissue, etc.) larger than the drainage ports and the drainage lumen to enter the interstitial drainage cavities and/or channels, the relatively larger entry port size allows for decreasing the suction force applied to the wall of the organ being drained. This decreased force prevents unnecessary damage to the organ wall. In some embodiments, the membrane may also have portions, in the expanded state, that have a plurality of perforations wherein the individual perforations in the membrane have an equal or smaller cross sectional area than that of the drainage ports and the drainage lumen so that debris smaller than the perforations can pass through the membrane, the drainage ports, and the drainage lumen without obstructing either. Debris larger than the perforations is stopped by the membrane while still leaving a plurality of perforations in the membrane unblocked, thus creating a drainage system in parallel rather than in series. Due to there being a plurality of perforations in a portion of the membrane of these embodiments, the suction force produced by the drainage ports is distributed amongst all the perforations, thus mitigating the detrimental effects of suction force on the tissues of the body cavity being drained. This FMID catheter is particularly advantageous when patients require an indwelling catheter and/or are at risk of having a catheter obstruction. Because the presently disclosed device improves the basic function of current Foley catheters without changing the way it is implemented by the health care professional, it is expected to replace the current Foley catheters as the standard of care.

BRIEF DESCRIPTION OF THE DRAWINGS

Further advantages of the invention will become apparent by reference to the detailed description of preferred embodiments when considered in conjunction with the drawings which form a portion of the disclosure and wherein.

DETAILED DESCRIPTION

The following detailed description is presented to enable any person skilled in the art to make and use the invention. For purposes of explanation, specific details are set forth to provide a thorough understanding of the present invention. However, it will be apparent to one skilled in the art that these specific details are not required to practice the invention. Descriptions of specific applications are provided only as representative examples. Various modifications to the preferred embodiments will be readily apparent to one skilled in the art, and the general principles defined herein may be applied to other embodiments and applications without departing from the scope of the invention. The present invention is not intended to be limited to the embodiments shown, but is to be accorded the widest possible scope consistent with the principles and features disclosed herein.

Figure 1:
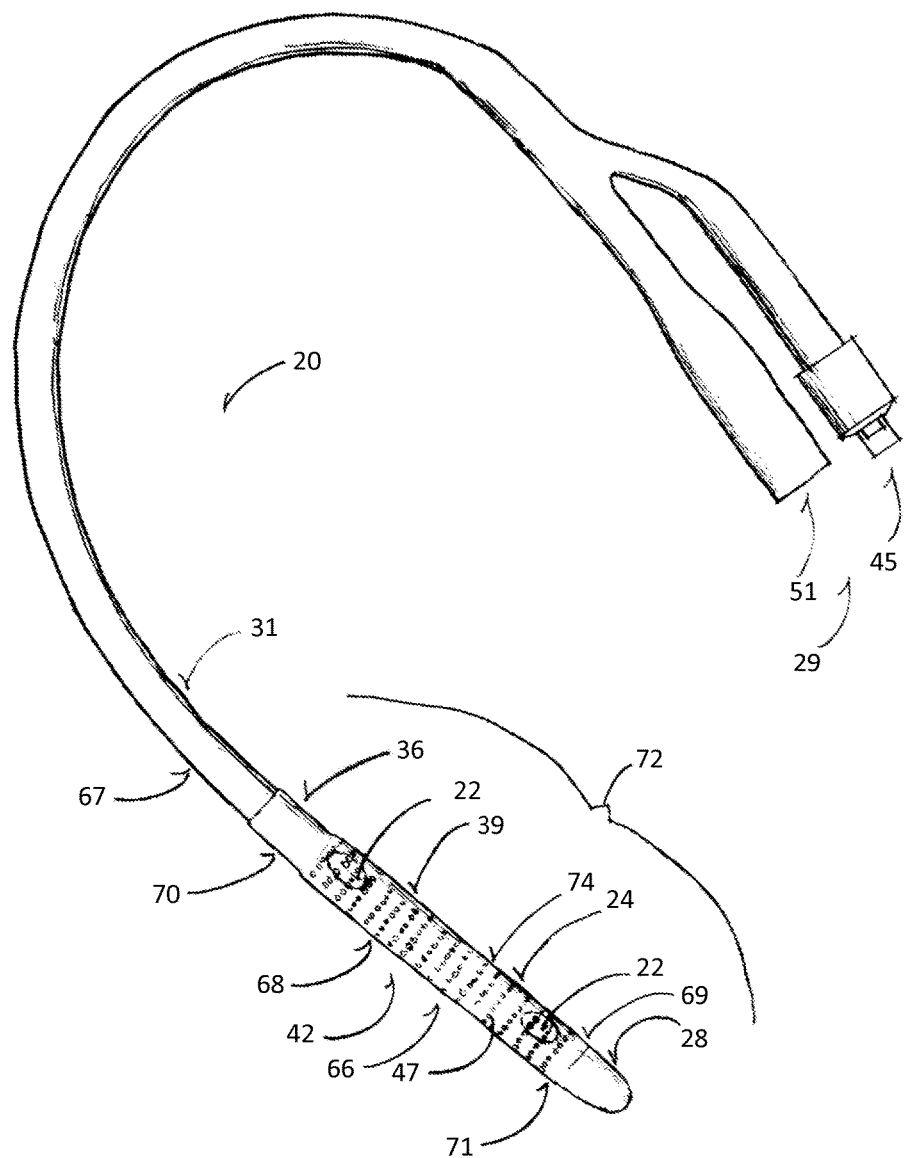
FIG. 1 depicts a pictorial view of an embodiment of a FMID catheter in a collapsed state.
Figure 2:
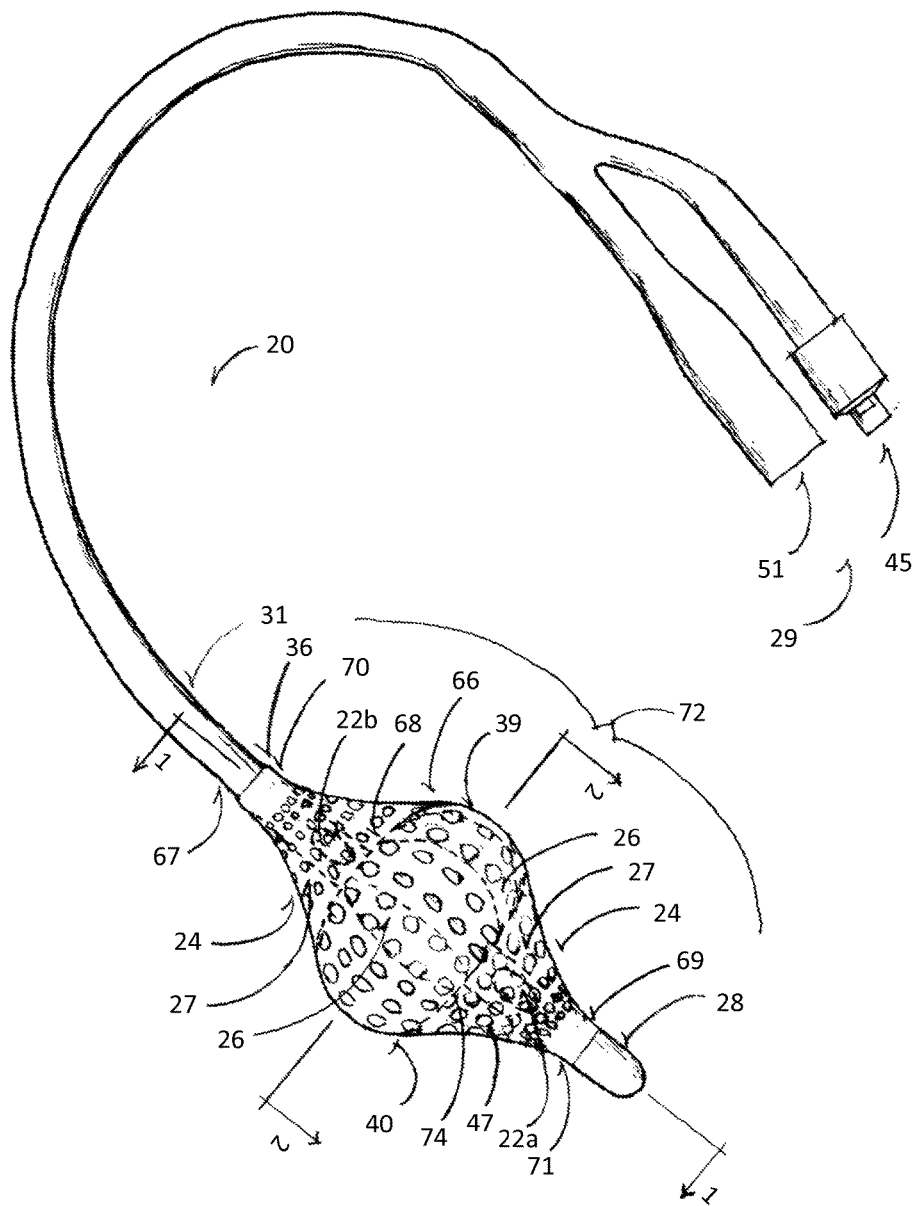
FIG. 2 depicts a pictorial view of an embodiment of a FMID catheter in an expanded state.

For the purposes of this disclosure a Foley retention drainage catheter, which may be interchangeably referred to as a Foley catheter or drainage catheter, and is commonly used to drain a human bladder, is discussed. However it should be understood that the same inventive features described in this disclosure can be applied to other types of catheters used in other parts of the bodies of both animals and humans in need thereof. Referring to the drawings for a better understanding of the function and structure of the invention, FIGS. 1 and 2 present an exemplary embodiment of the multi-lumen filter membrane internal interstitial drainage channel catheter 20, referred to also as a FMID catheter 20. As shown in FIG. 1, the FMID catheter 20 is an improvement over the existing Foley catheter design. Like the existing Foley catheter, the FMID catheter 20, is designed to be inserted into a body cavity 21 of a patient in need thereof, which may include a human being or another animal. Once inserted, the FMID catheter 20 can be used to drain fluids from, remove small debris from, and/or infuse fluids into of the body cavity 21. In an exemplary embodiment, the FMID catheter 20 is an indwelling catheter that is inserted through the urethral canal 58, and in some cases the suprapubic tract, and then into the bladder 59. It should be understood that the dimensions of the FMID catheter 20 and its components can vary both as to length and diameter as needed or appropriate for a given procedure on a patient in need of draining a body cavity 21.

Figure 3:
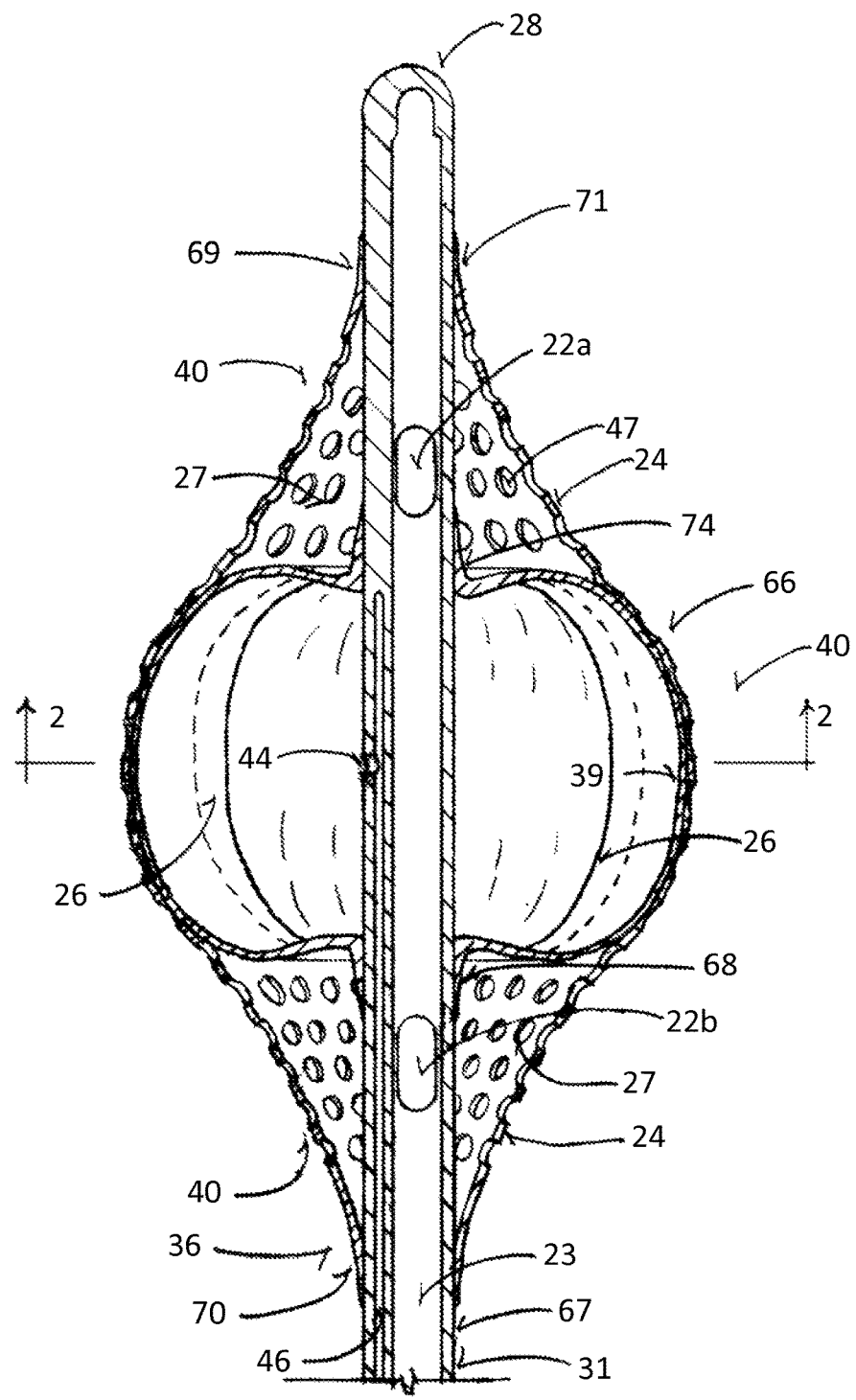
FIG. 3 depicts an enlarged sectioned view of the distal portion of the FMID catheter shown in FIG. 2 taken along LINE 1-1.
Figure 4:
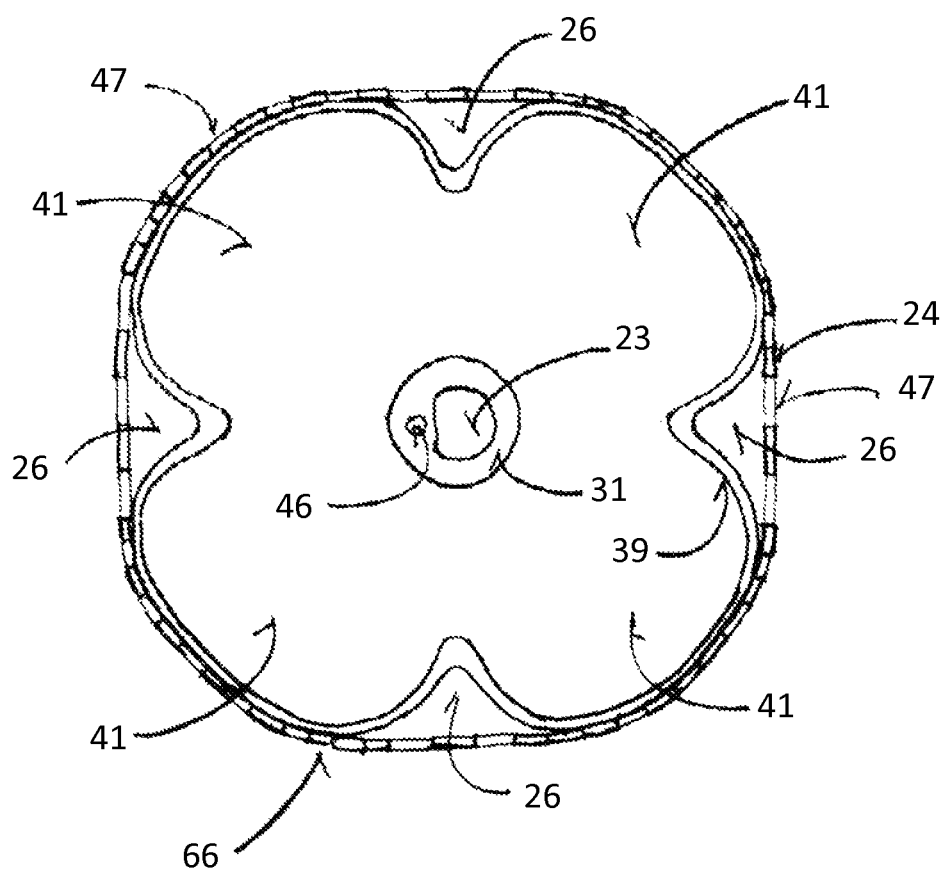
FIG. 4 depicts an enlarged sectioned view of the distal portion of the FMID catheter shown in FIG. 2 taken along LINE 2-2.
Figure 5:
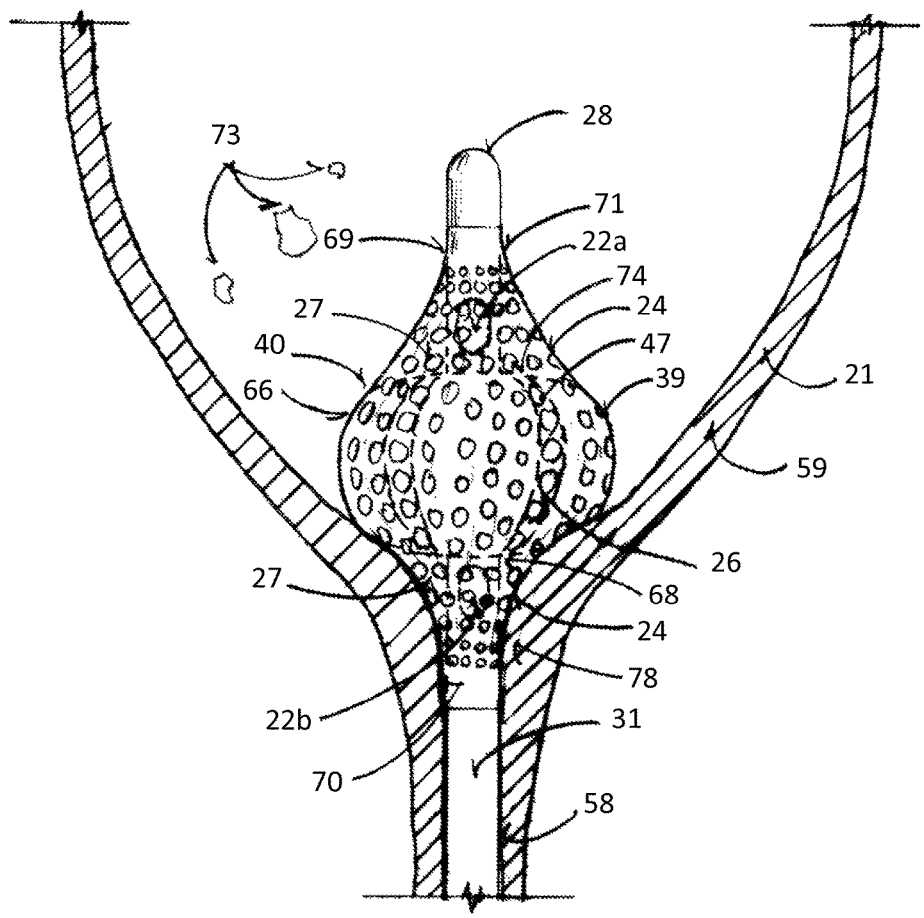
FIG. 5 depicts an embodiment of a FMID catheter in an expanded state positioned in a body cavity of a patient.

FIG. 3 depicts an enlarged sectioned view of the distal portion 72 of the embodiment of a FMID catheter 20 shown in FIG. 2 along LINE 1-1. FIG. 4 depicts an enlarged sectioned view of the distal portion 72 of the embodiment of a FMID catheter 20 shown in FIG. 2 along LINE 2-2. FIG. 5 depicts an exemplary embodiment of a FMID catheter 20 positioned in a body cavity 21 (the bladder 59, as shown) of a patient. Once the FMID catheter 20 is in position, the segmented retention element 39 surrounding a portion of the distal end 28 of the FMID catheter 20 is expandable for inflation to the expanded state 40 and retains the FMID catheter 20 against the neck 78 of the bladder 59 until the segmented retention element 39 is deflated for removal (the distal end 28 being the end of the catheter inserted into the body cavity 21 and the proximal end 29 being the end that remains outside of the body). Although segmented retention elements are preferred in many embodiments, it should be understood that some embodiments may include non-segmented expandable retention element 39. Unless specifically stated otherwise, it should be understood that the discussed embodiments could include either a segmented or non-segmented retention element 39. When included, the segmented retention element 39 can have an unlimited number of segments and/or as few as one segment. Preferred embodiments contain four symmetrical segments. The distal end 28 of a flexible elongated cylindrical element 31 can be of hemispherical shape and/or other shapes as required per conditions specific to its intended use by a medical professional. Pluralities of lumina (drainage lumen 23, inflation lumen 46, and irrigation lumen 48) provide for functions comprising, but not limited to, separate drainage, inflation, and irrigation, respectively. Preferred embodiments of the FMID catheter 20 will have at least two lumina (drainage lumen 23 and inflation lumen 46). In addition to the aforementioned characteristics, the FMID catheter 20 provides for a perforated filter membrane 24 encapsulating the retention element 39. In some embodiments, however, the filter membrane 24 may be configured to not encapsulate any of the segmented retention element 39. The perforated filter membrane 24 is also disposed over the proximal drainage ports 22*b* and over the distal drainage ports 22*a* of the drainage lumen 23 of the FMID catheter 20. When in an expanded state 40 the filter membrane 24 mitigates the chance of the drainage ports 22, drainage lumen 23, and drainage connector 51 of the FMID catheter 20 being obstructed by debris 73.

To retain the FMID catheter 20 in a body cavity 21 of a patient in need thereof, a segmented retention element 39 comprising one or more substantially spherical wedges 41 is disposed near the distal end 28 but proximal to the distal drainage ports 22*a* and distal to the proximal drainage ports 22*b*. For example, see FIG. 3. One or more inflation ports 44 are disposed on the flexible elongated cylindrical element 31 underneath the segmented retention element 39. An inflation lumen 46 is disposed within the elongated cylindrical element 31 from the inflation ports 44 to the proximal end 29 of the elongated cylindrical element 31. In preferred embodiments, the inflation lumen 46 is positioned adjacent to the drainage lumen 23 and extending longitudinally within the elongated cylindrical element 31. One or more inflation valves 45 are disposed at or near the proximal end 29. The valve(s) 45 can be of various forms known in the art. The segmented retention element 39 is in fluid communication with the inflation ports 44. The inflation ports 44 communicate with the inflation lumen 46. The inflation lumen 46 communicates with the inflation valve 45. A removable syringe (not shown) communicating with the inflation valve 45 can be used to exert a positive pressure force on the segmented retention element 39, thereby causing inflation to an expanded state 40 of the segmented retention element 39. Similarly, a removable syringe (not shown) communicating with the inflation valve 45 can be used to exert a negative pressure force on the segmented retention element 39, thereby causing deflation to a collapsed state 42 of the segmented retention element 39. Inflation of the segmented retention element 39 can be carried out by injecting air, gel, fluid, or other substance known in the art. Preferably, a biocompatible fluid, such as saline, water, and/or contrast media, is used to inflate the segmented retention element 39. Alternatively, the segmented retention element 39 and/or the filter membrane 24 of the FMID catheter 20 can be mechanically expandable.

To drain the body cavity 21 of the patient, the FMID catheter 20 includes a drainage lumen 23 extends longitudinally within the flexible elongated cylindrical element 31 and having a drainage connector 51 at the proximal end 29 of the elongated cylindrical element. Preferably, the drainage lumen 23 is disposed centrally within the elongated cylindrical element 31. The drainage ports 22 can be of any size and/or shape and disposed anywhere along the elongated cylindrical element 31. Preferably, the drainage lumen 23 may have one or a plurality of drainage ports 22 disposed at least near the distal end 74 of the retention element 39 in fluid communication with the exterior, (e.g., the body cavity 21 to be drained) of the FMID catheter 20. In embodiments having a double-cone configuration, these preferably also have one or a plurality of drainage ports 22 disposed at least near the proximal end 68 of the retention element 39 in fluid communication with the exterior, (e.g., the body cavity 21 to be drained) of the FMID catheter 20.

To mitigate the risk of obstruction to the drainage lumen 23 and the drainage ports 22, a filter membrane 24 is included with its proximal end 36 affixed on the outer surface 67 of the flexible elongated cylindrical element 31 near the proximal end 68 of the retention element 39 and disposed proximal to the proximal drainage ports 22*b* (referred to as the proximal membrane affixing point 70). The distal end 69 of the filter membrane 24 is affixed on the outer surface 67 of the elongated cylindrical element 31 near the distal end 28 and disposed distal to the distal drainage ports 22*a* (referred to as the distal membrane affixing point 71). The retention element 39 is preferably made of a soft and resilient material capable of expansion and deflation, such as silicone, latex rubber, synthetic latex, silicone-based composite materials, latex-based composite materials, and/or combinations of these. Such materials will stretch or expand to the expanded state of the device and then retract to the collapsed state of the device. It should be understood that the retention element 39 may be made of any acceptable material known in the art or later discovered to be acceptable for constructing similar balloon catheters.

When the retention element 39 and the filter membrane 24 are in a collapsed state 42, the retention element 39 and the filter membrane 24 lay substantially flat against the flexible elongated cylindrical element 31 encapsulating but not affixed to the remaining portion of the retention element 39 or the elongated cylindrical element 31 between the proximal membrane affixing point 70 and distal membrane affixing points 71. Some embodiments of the FMID catheter 20 may include a portion of the elongated cylindrical element 31, for example, but not intended to be limiting in any way, from one end of the retention element 39 to the distal membrane affixing points 71 (i.e., substantially all of the portion inserted into the body cavity 21), that is made of a firm and resilient material, such as biocompatible plastics or other materials known in the art. The firm and resilient material can be disposed continuously or in a series of rings within the aforementioned portion. It is understood that any other material and configuration of material that increases the stiffness of the catheter 20 at the aforementioned portion is contemplated. Thus, the FMID catheter 20 is to be inserted into a body cavity 21 when in the collapsed state 42.

When the retention element 39 is in the expanded state 40, the filter membrane 24 is expanded into a substantially double conical shape being largest in diameter near the retention element 39, and smallest in diameter at proximal membrane affixing point 70 and distal membrane affixing points 71. This configuration causes the filer membrane 24 to be held apart from the flexible elongated cylindrical element 31 to form internal interstitial drainage cavities 27, one disposed near the proximal end 68 of the retention element 39 (27a) and one disposed near the distal end 28 of the elongated cylindrical element 31 (27b), between the filter membrane 24 and the elongated cylindrical element 31. The proximal 27a and distal 27b internal interstitial drainage cavities 27 are in fluid communication with the proximal 22b and distal drainage ports 22a, respectively, to allow for fluids and/or debris to flow into the drainage ports 22. The internal interstitial drainage cavities 27 can be formed by masses, elements, and/or processes different from those relating to the retention element 39 and/or the filter membrane 24.

The filter membrane 24 has a plurality of perforations 47 that are individually smaller in cross sectional area than the most constricted portion of the drainage lumen 23 and the drainage ports 22 whereby preventing debris 73 larger than the most constricted portion of the drainage lumen 23 and the drainage ports 22 from entering an internal interstitial drainage cavities 27. When the retention element 39 and the filter membrane 24 are in the expanded state 40 a plurality of sizes and shapes of perforations 47 may result. Debris 73 smaller in cross sectional area than the cross sectional area of an individual perforation 47, and thus smaller than the most constricted portion of the drainage lumen 23 and the drainage ports 22, can pass freely through the filter membrane 24, drainage ports 22, and then through the drainage lumen 23 without causing obstruction. As the plurality of perforations 47 in the filter membrane 24 provide a significantly greater total cross sectional drainage area than the total cross sectional drainage area of the drainage ports 22 and the drainage lumen 23 so that when debris 73 larger than the perforations lodges in and/or over more than one perforation 47, the rate of drainage is not substantially diminished or obstructed due to the availability of a plurality of perforations 47. In the event that debris 73 does cover the filter membrane 24, a removable syringe (not shown) can be connected to the drainage connector 51. A negative pressure force can be applied, by use of the removable syringe, to the perforations 47 to aspirate debris 73 through the perforations 47, through the internal interstitial drainage cavities 27, through the internal interstitial drainage channels 26, through the drainage ports 22, and through the drainage lumen 23. A positive pressure force can be applied, by use of the removable syringe, to the perforations 47 to flush debris 73 out of and/or away from the perforations 47.

The filter membrane 24 may include perforations 47 that are round in shape and/or any other shape and may be of varying size. In addition to or in the alternative to a plurality of perforations 47, some embodiments of the FMID catheter 20 may include a filter membrane 24 comprising a material with passive diffusion characteristics that would allow the free flow of fluids and dissolved materials through the membrane while blocking debris 73. Other embodiments may include a filter membrane 24 having a configuration and/or construction that does not possess the qualities and/or characteristics of a membrane, such as, but not intended to be limiting, open cell foam and/or sponge materials could be utilized. The distal end 69 of the filter membrane 24 can be non-perforated. The filter membrane 24 may additionally have ribs (not shown) extending from the proximal membrane affixing point 70 to the distal membrane affixing point 71 to provide structural support for the filter membrane 24 while in the expanded state 40.

Due to there being a plurality of perforations 47 in the filter membrane 24, the suction force produced by the drainage ports 22 is dispersed amongst all the perforations 47, thus resulting in a greatly reduced rate of fluid flowing through any individual perforation 47 as compared to the rate of fluid flowing through any individual drainage port 22. Thus, a significant suction force is not created by individual perforations 47. This characteristic causes debris 73 to not be readily drawn to the filter membrane 24, as it would be drawn to an unfiltered drainage port, which reduces the chance of debris buildup on the filter membrane 24. This characteristic also reduces the detrimental effects of focal suction force projected on the tissues of the body cavity 21 being drained, particularly the bladder mucosa 32, the irritation of which can cause an increased risk of catheter associated UTIs and/or other damage to the mucosa. Catheter associated UTIs are now the most expensive hospital acquired infection according to the Centers for Disease Control and Prevention (CDC).

To provide for enhanced drainage when the segmented retention element 39 and filter membrane 24 are in their expanded state 40, expandable internal interstitial drainage cavities 27 are created between the filter membrane 24 and the flexible elongated cylindrical element 31, which expand as the filter membrane is pushed away from the elongated cylindrical element 31. Also, when the segmented retention element 39 and filter membrane 24 are in their expanded state 40, expandable internal interstitial drainage channels 26 are created between the spherical wedges 41 of the retention element 39 and the filter membrane 24. The internal interstitial drainage channels 26 are disposed from the distal end 74 of the segmented retention element 39 to the proximal end 68 of the segmented retention element 39 and expand proportionally as the expanded state of the segmented retention element 39 and the filter membrane 24 is reached. The internal interstitial drainage channels 26 can be formed by masses, elements, and/or processes different from those relating to the retention element 39 and/or the filter membrane 24. As stated above, the drainage ports 22 are in fluid communication with the internal interstitial drainage cavities 27. The internal interstitial drainage cavities 27 are in fluid communication with the internal interstitial drainage channels 26. The internal interstitial drainage cavities 27 and/or the internal interstitial drainage channels 26 are in fluid communication with the body cavity 21 being drained through the filter membrane 24. The internal interstitial drainage channels 26 advantageously allow for more surface area of the distal portion 72 of the FMID catheter 20 to drain the body cavity 21, as well as fluid communication between the internal interstitial drainage cavities 27. This configuration also advantageously allows for continued drainage through one drainage port 22 in the event that the other becomes obstructed.

Figure 6:
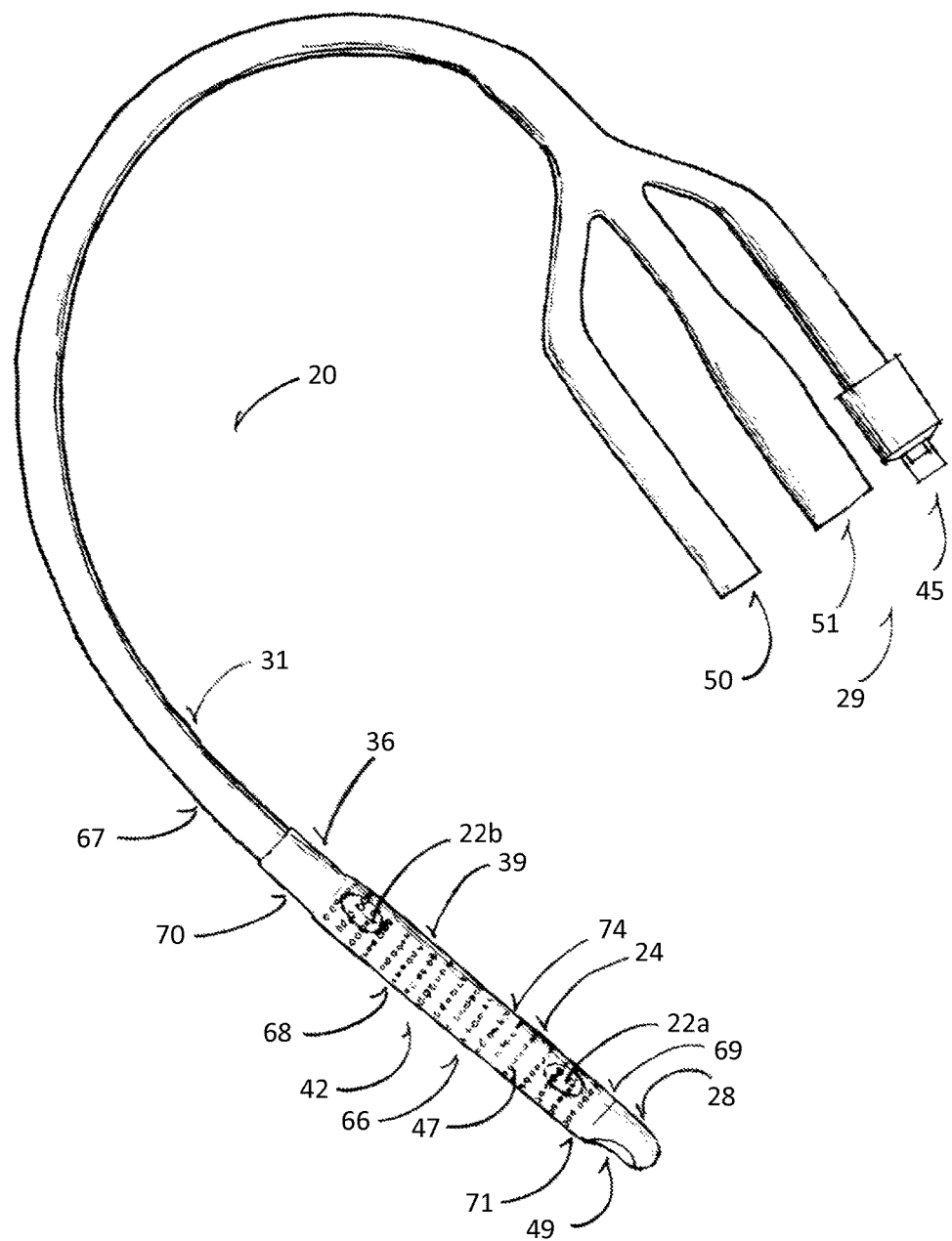
FIG. 6 depicts a pictorial view of an embodiment of a FMID catheter in a collapsed state with irrigation port and irrigation opening connector.
Figure 7:
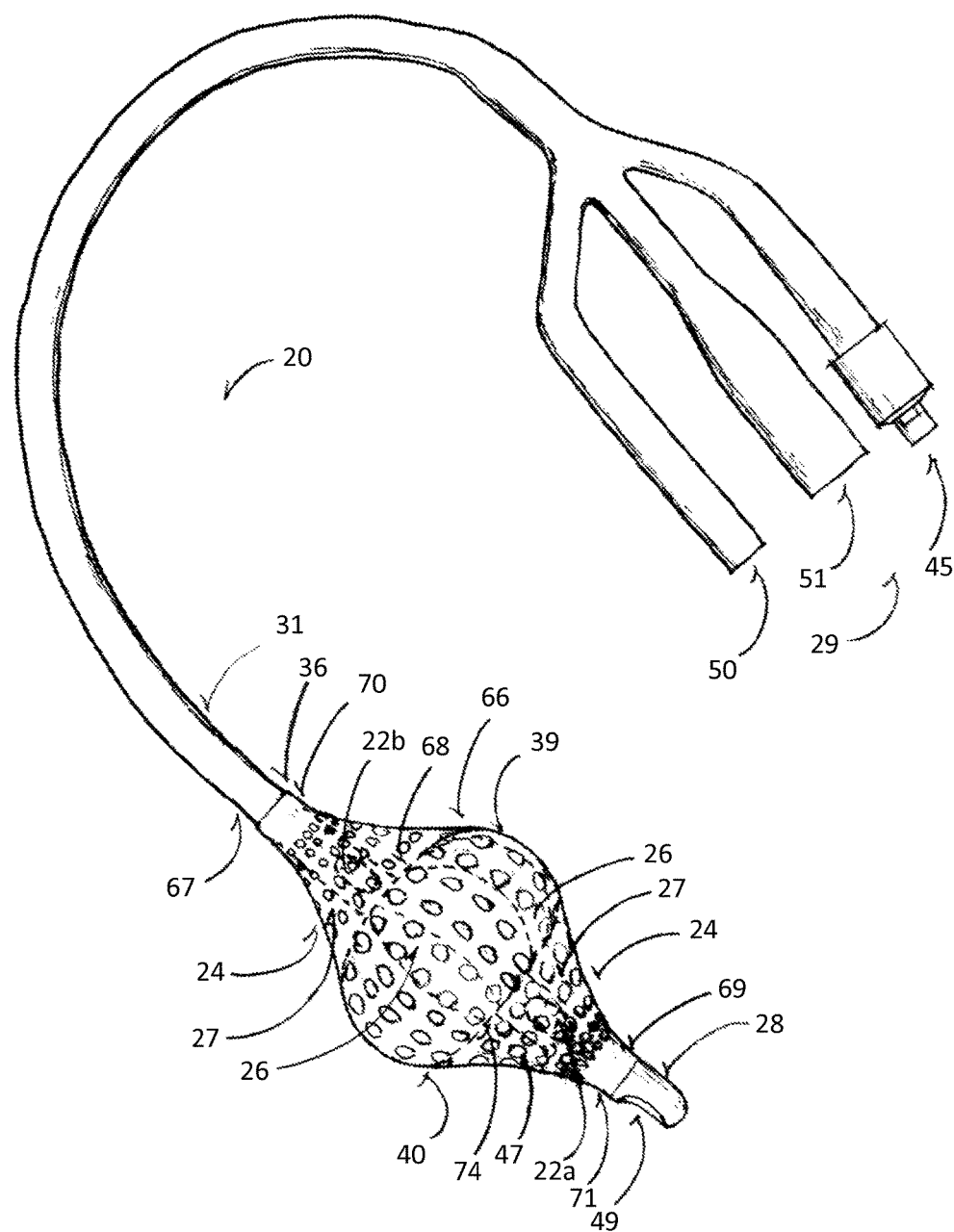
FIG. 7 depicts a pictorial view of an embodiment of a FMID catheter in an expanded state with irrigation port and irrigation opening connector.

Some embodiments of the FMID catheter 20 may have an irrigation lumen 48 disposed in the flexible elongated cylindrical element 31 and extending longitudinally within the elongated cylindrical element 31, having an irrigation opening connector 50 at the proximal end 29 of the elongated cylindrical element 31. The irrigation lumen 48 may have one or more irrigation ports 49 disposed along the elongated cylindrical element 31. The irrigation port(s) 49 can be of any size and/or shape and disposed anywhere along the elongated cylindrical element 31. Preferably, the irrigation port(s) 49 at and/or near the distal end 28, in fluid communication with the exterior 66 of the FMID catheter 20, and located distal to the filter membrane 24 for delivering an irrigating solution to the body cavity 21 being drained. FIGS. 6 and 7 depict a pictorial view of illustrative embodiment of a FMID catheter 20 having an irrigation lumen 48. A normal saline and/or sterile water irrigating fluid may be delivered to the body cavity 21 in order to prevent postoperative and/or spontaneous blood clot retention. The irrigating fluid may also be delivered to the body cavity 21 being drained to cleanse and/or administer medicines for treating conditions, such as bacteriuria.

Figure 8:
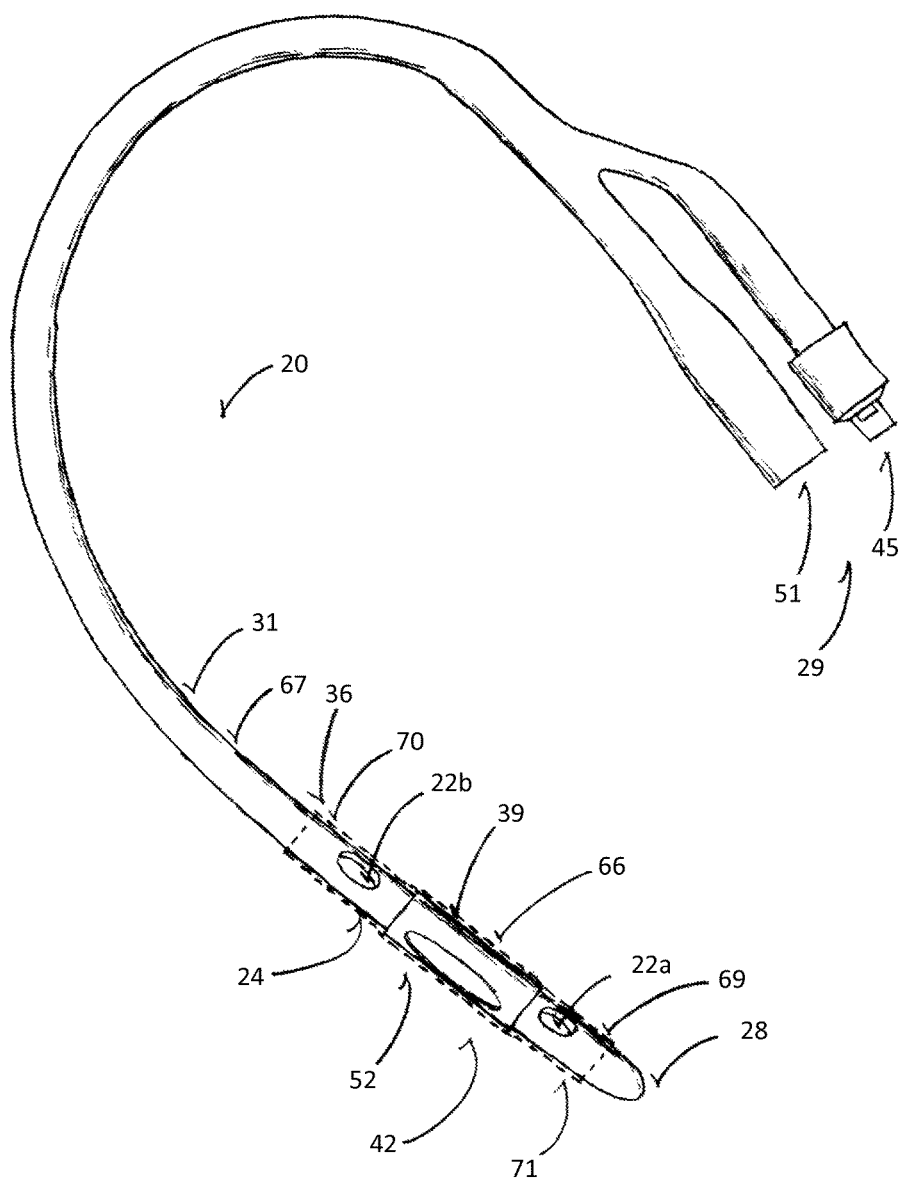
FIG. 8 depicts a pictorial view of an embodiment of a FMID catheter in a collapsed state with perforated sleeve.
Figure 9:
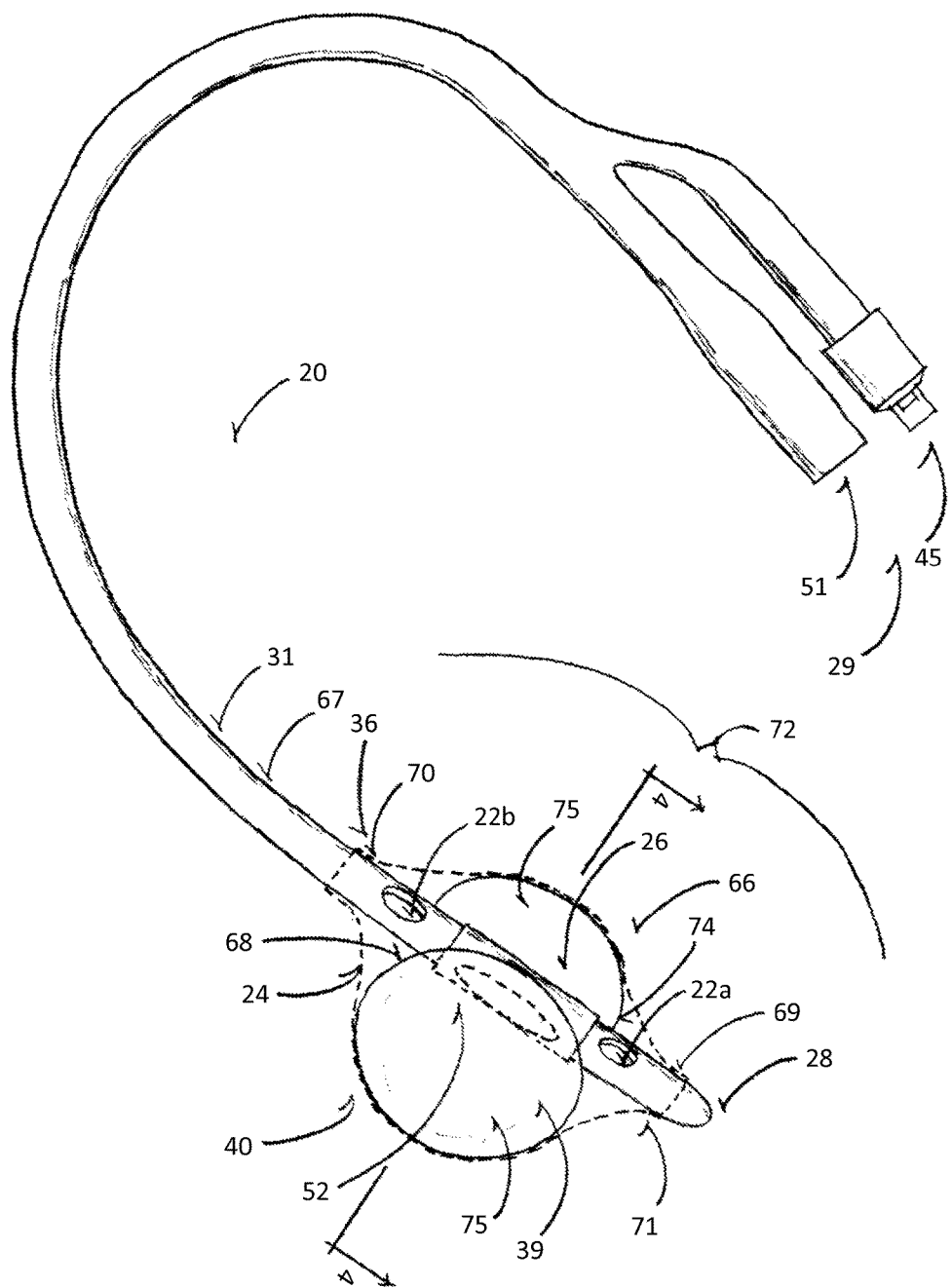
FIG. 9 depicts a pictorial view of an embodiment of a FMID catheter in an expanded state with perforated sleeve.
Figure 10:
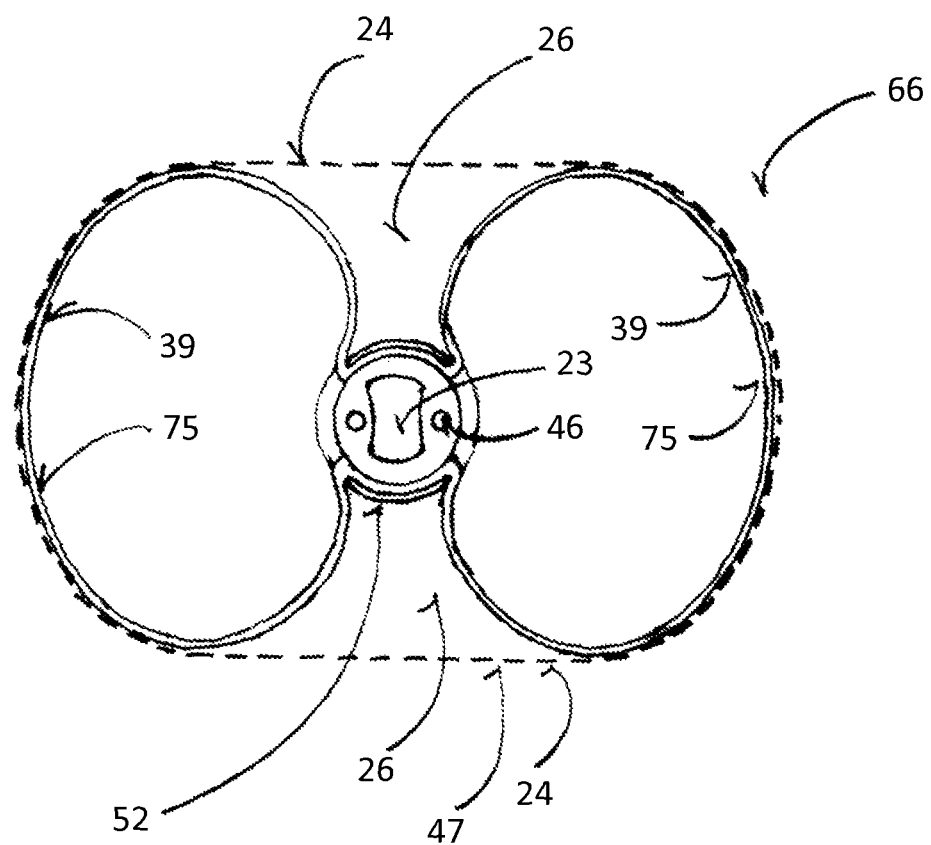
FIG. 10 depicts an enlarged sectioned view of the distal portion of the FMID catheter shown in FIG. 9 taken along LINE 4-4.

Other embodiments of FMID catheter 20 may have a plurality of separate sub-retention elements 75 in the segmented retention element 39 that are formed by disposing a perforated sleeve 52 around the collapsed retention element 39. When being put into an expanded state, the retention element 39 expands through the perforations in the perforated sleeve 52 creating one and or more sub-retention elements 75. FIGS. 8 and 9 depict a pictorial view of a FMID catheter 20 having a perforated sleeve 52 and sub-retention elements 75. FIG. 10 depicts an enlarged sectioned view of the distal portion 72 of the embodiment of a FMID catheter 20 shown in FIG. 9 along LINE 4-4. The separate sub-retention elements 75 in the segmented retention element 39 due to the perforated sleeve 52 may create larger interstitial drainage channels 26.

Some embodiments of the FMID catheter 20 may have at least one drainage port 22c disposed at the distal end 28 of the flexible elongated cylindrical element 31. This configuration permits the catheter 20 to be inserted over a guidewire 57 through the drainage lumen 23 and the aforementioned drainage port 22c disposed on the distal end 28. This configuration is especially useful in various surgical procedures, such as those needing cystoscopic access to the bladder 32 or body cavity 21 with subsequent need for leaving a catheter in situ. A guidewire 57 is placed under direct vision using a cystoscope. The cystoscope is removed leaving the guidewire 57 in place within the bladder 32 or body cavity 21, on which the catheter, such as FMID catheter 20, may be guided.

Figure 11:
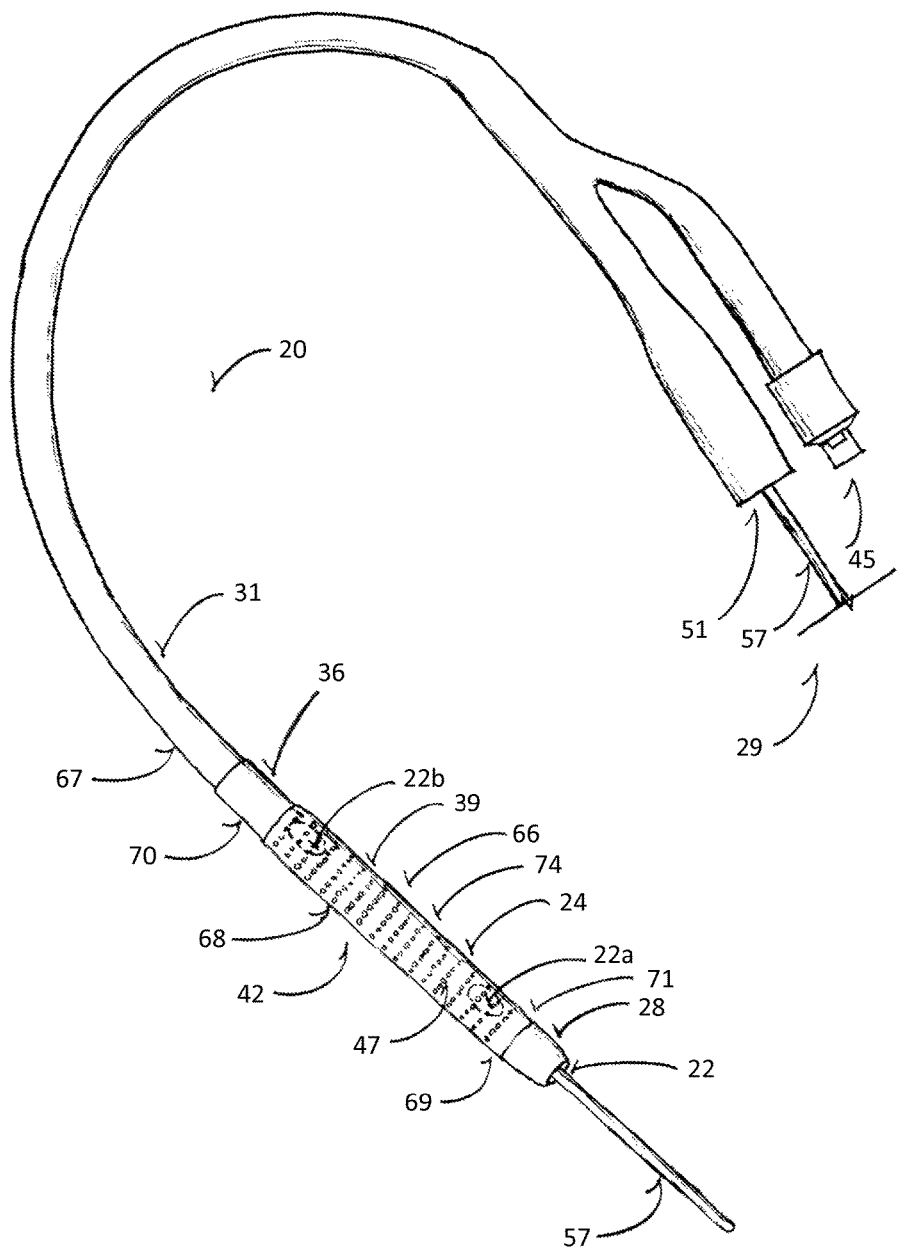
FIG. 11 depicts a pictorial view of an embodiment of a FMID catheter in a collapsed state with wire guide.

In addition, endoscopic instruments and other medical devices, for example, but not limited to cystoscopes, ureteroscopes, temperature probes, microwave thermotherapy probes, radiofrequency ablation probes, urodynamic catheters, etc. can likewise be inserted through the FMID catheter 20 using drainage lumen 23 (with or without the aid of guidewire 57) for access to the bladder 32 or body cavity 21. FIG. 11 depicts a pictorial view of a FMID catheter 20 as described in this embodiment.

Figure 12:
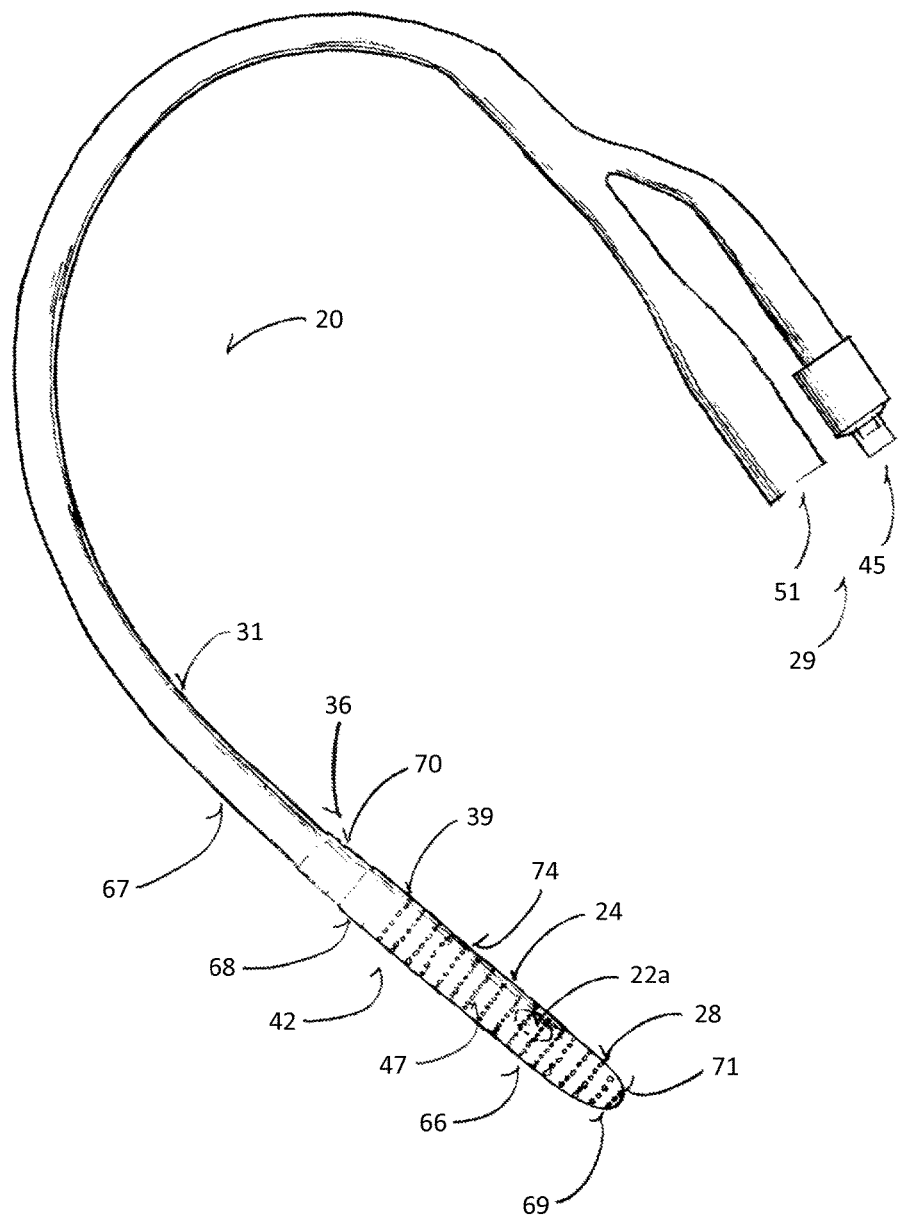
FIG. 12 depicts a pictorial view of an embodiment of a FMID catheter in a collapsed state with encapsulated distal end.
Figure 13:
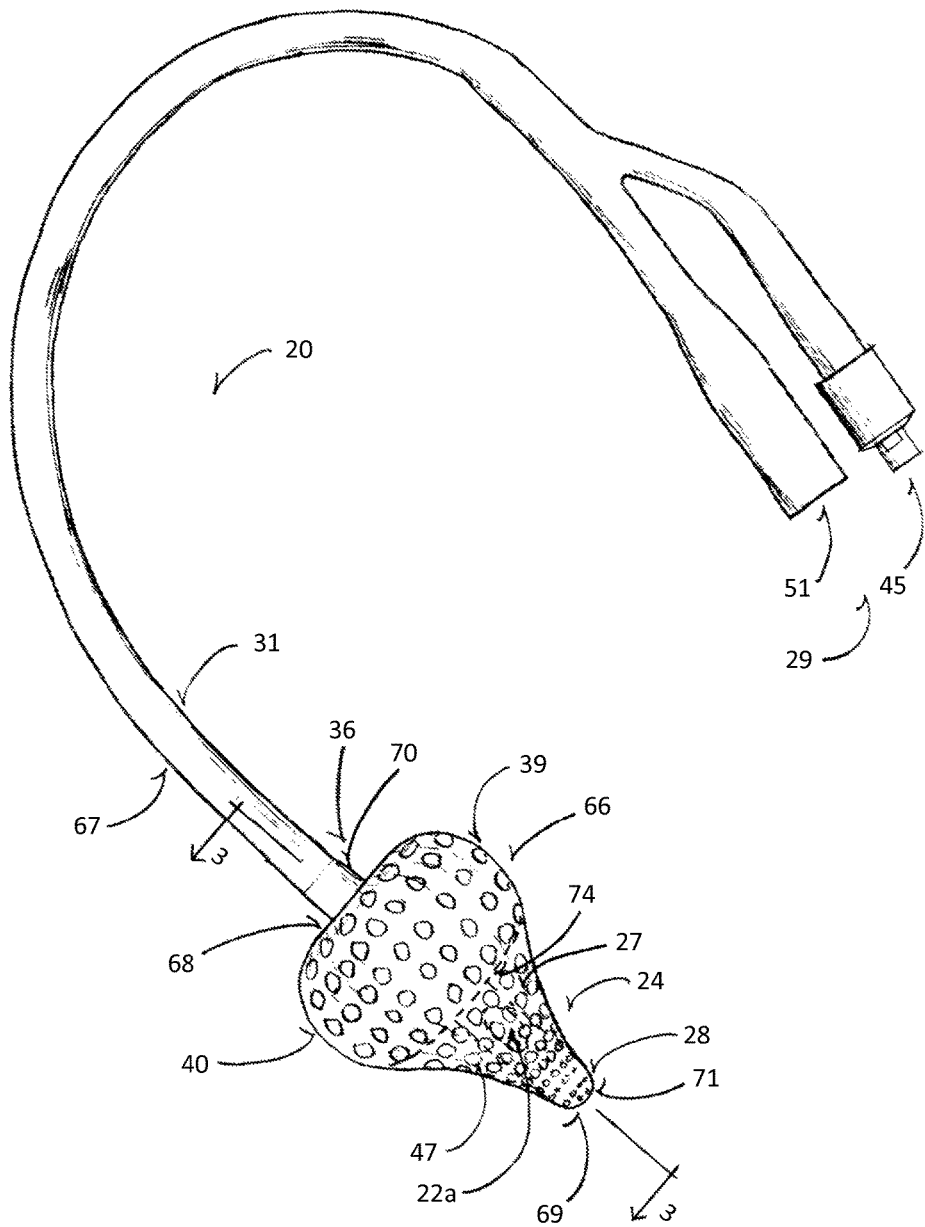
FIG. 13 depicts a pictorial view of an embodiment of a FMID catheter in an expanded state with encapsulated distal end.
Figure 14:
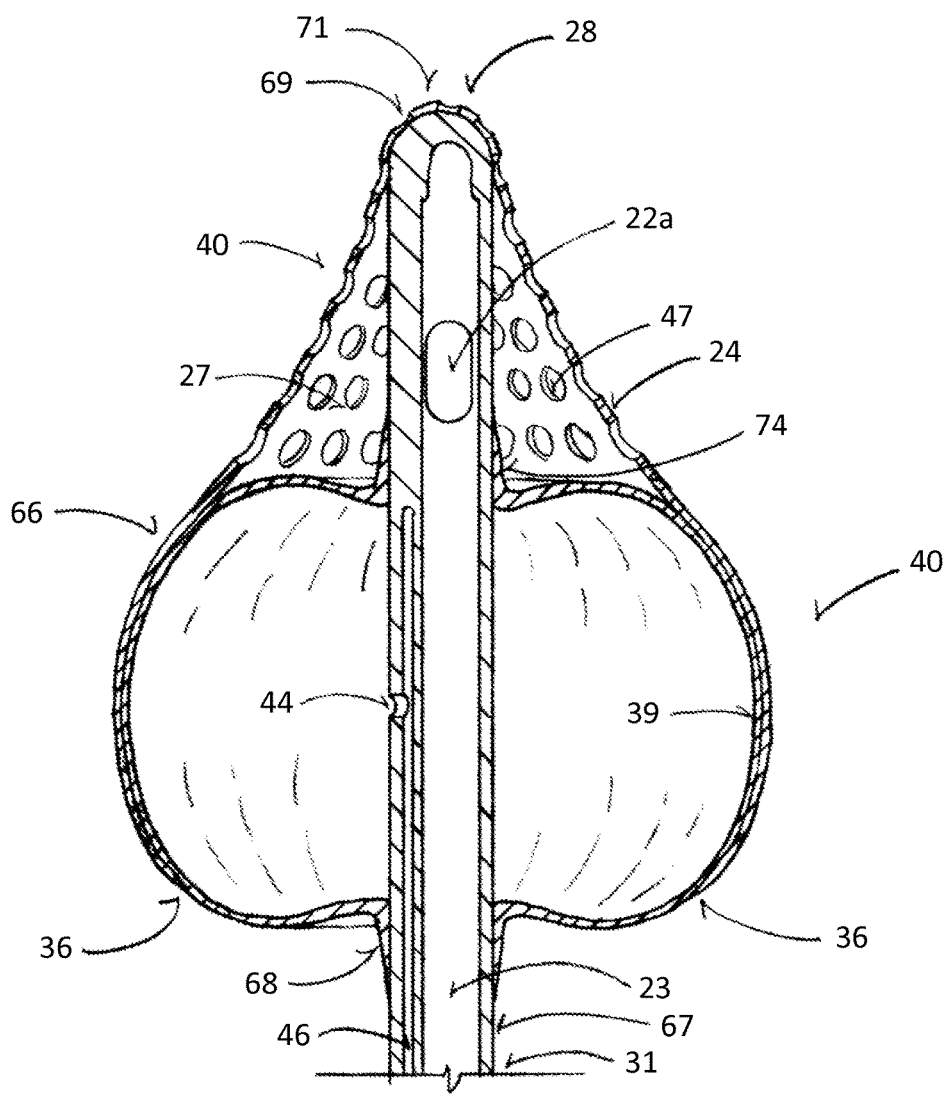
FIG. 14 depicts an enlarged sectioned view of the distal portion of the FMID catheter shown in FIG. 13 taken along LINE 3-3.

Further embodiments of the FMID catheter 20 may include a distal membrane affixing point 71 of the filter membrane 24 disposed at the distal end 28 of the flexible elongated cylindrical element 31 such that the distal membrane affixing point 71 seats into and encapsulates the distal end 28. The distal membrane affixing point 71 of the filter membrane 24 may and/or may not be perforated. FIGS. 12 and 13 depict a pictorial view of a FMID catheter 20 as described in this embodiment. Furthermore, some embodiments may include a filter membrane 24 configured to encapsulate only a portion of the segmented retention element 39. FIG. 14 depicts an enlarged sectioned view of the distal portion of a FMID catheter with a partially encapsulating filter membrane. Thus, in some embodiments, the proximal membrane affixing point 70 may be on the proximal end 68 of the retention element 39. Note that no proximal drainage port 22b is necessary in this embodiment. Nevertheless, a segmented retention element 39 may be used to create internal interstitial drainage channels 26 and more surface area for drainage through the plurality of perforations 47.

Figure 15:
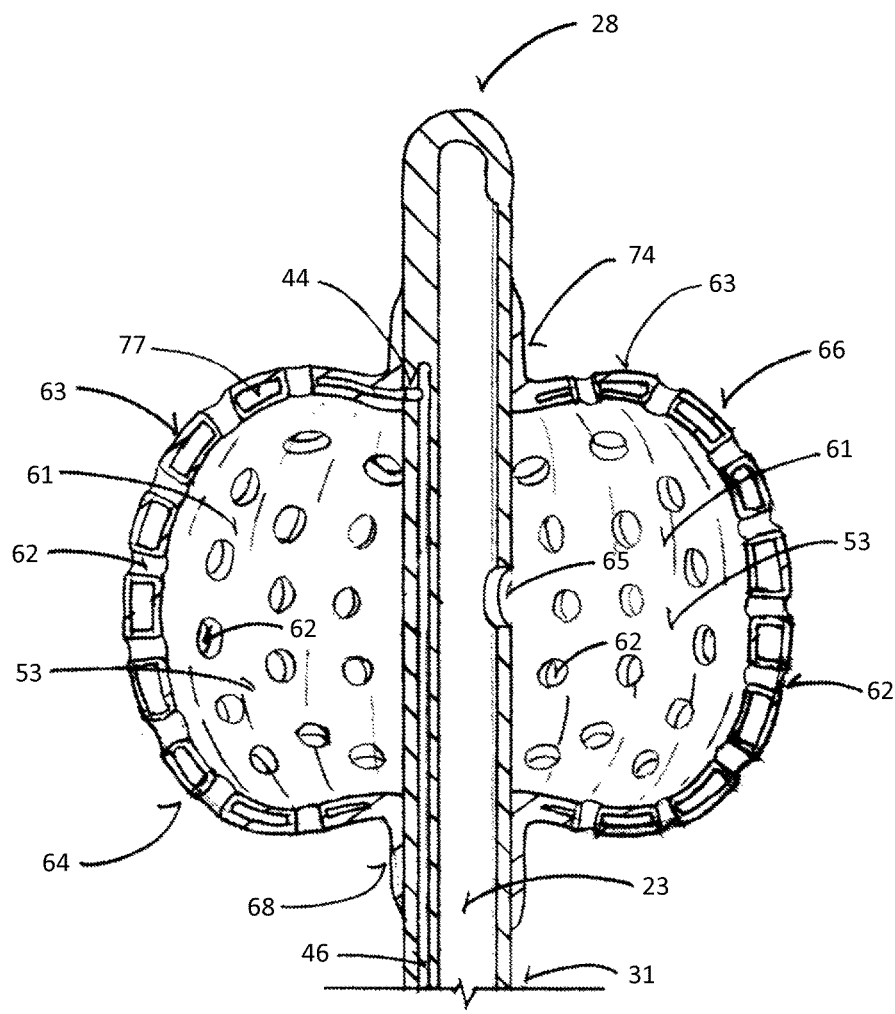
FIG. 15 depicts an enlarged sectioned view of an embodiment of a FMID catheter in an expanded state.

Still further embodiments of the FMID catheter 20 may include a perforated retention element 64 of which the perforations 47 are configured as drainage lumina 62. The perforated retention element 64 can be comprised of multiple layers. Disposed between the multiple layers of the perforated retention element 64 are inflation cavities 77 which are in fluid communication with the inflation port 44 and inflation lumen 46. The flexible elongated cylindrical element 31 (internal to the perforated retention element 64) may have one or more drainage ports 65 in fluid communication with the drainage lumen 23. Internal 53 to the perforated retention element 64 are drainage cavities 61 which are in fluid communication with the body cavity 21 being drained and the drainage port 65 and drainage lumen 23. It is also envisioned that the perforated retention element 64 can be comprised of a single layer that would be mechanically and/or by means other than inflation cavities deployed to an expanded state 40. The perforated retention element 64 would perform the job of both the segmented retention element 39 and the filter membrane 24 thus reducing the size of the unit so less patient discomfort is experienced. It could also reduce the cost and increase production efficiency. FIG. 15 depicts an enlarged sectioned view of a FMID catheter 20 having a perforated retention element 64.

Figure 16:
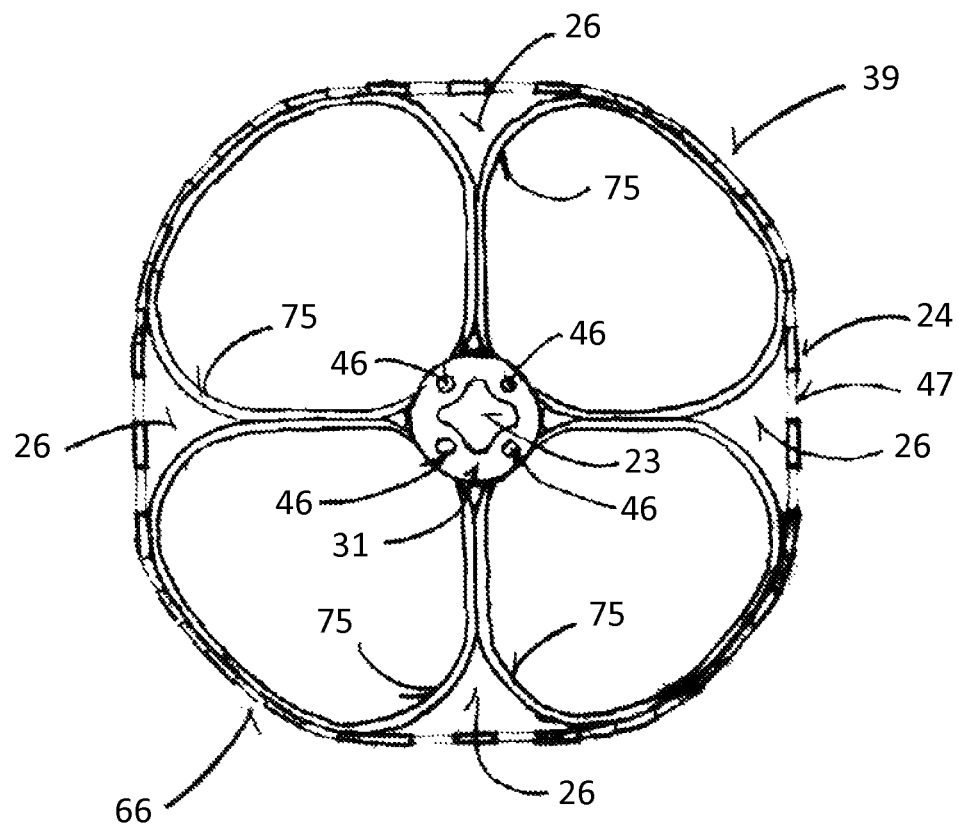
FIG. 16 depicts an enlarged sectioned view of an embodiment of a FMID catheter in an expanded state.

Still further embodiments of the FMID catheter 20 may include the retention element 39 comprised of one and or a plurality of individually inflated sub-retention elements 75. The sub-retention elements 75 can be disposed on the flexible elongated cylindrical element 31 radially, non-radially, and/or otherwise. In some embodiments, the sub-retention elements 75 can be inflated individually by separate inflation lumen 46. FIG. 16 depicts an enlarged sectioned view of the distal portion of a FMID catheter 20 having retention element 39 comprised four individually inflated sub-retention elements 75.

Figure 17A:
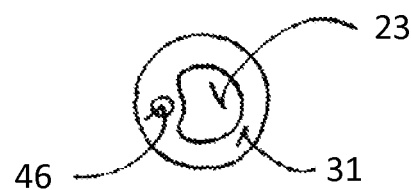
FIGS. 17A, B, and C depict enlarged sectioned views of the elongated cylindrical element of embodiments of a FMID catheter.
Figure 17B:
Figure 17C:
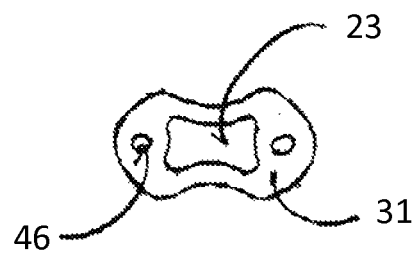
Figure 18:
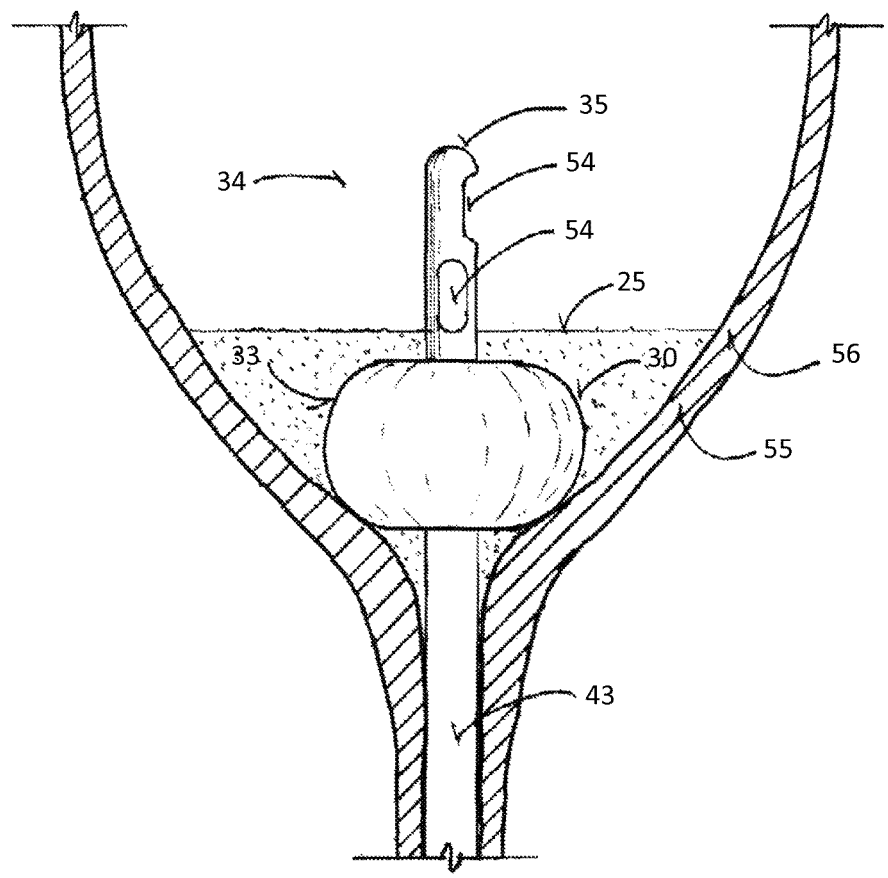
FIG. 18 depicts an exemplary PRIOR ART Foley retention drainage catheter.

It is to be understood that various embodiments of the FMID catheter 20 described above may also include one and or more of the following characteristics: The flexible elongated cylindrical element 31 of the FMID catheter 20 may take a shape other than cylindrical as required per conditions such as, but not limited to, trabeculated bladders, bladder diverticula, neobladders, and bladders with large prostate median lobes protruding into the bladder. FIGS. 17A-C depicts multiple sectional views of an elongated cylindrical element 31 having various internal structural shapes.

Figure 19:
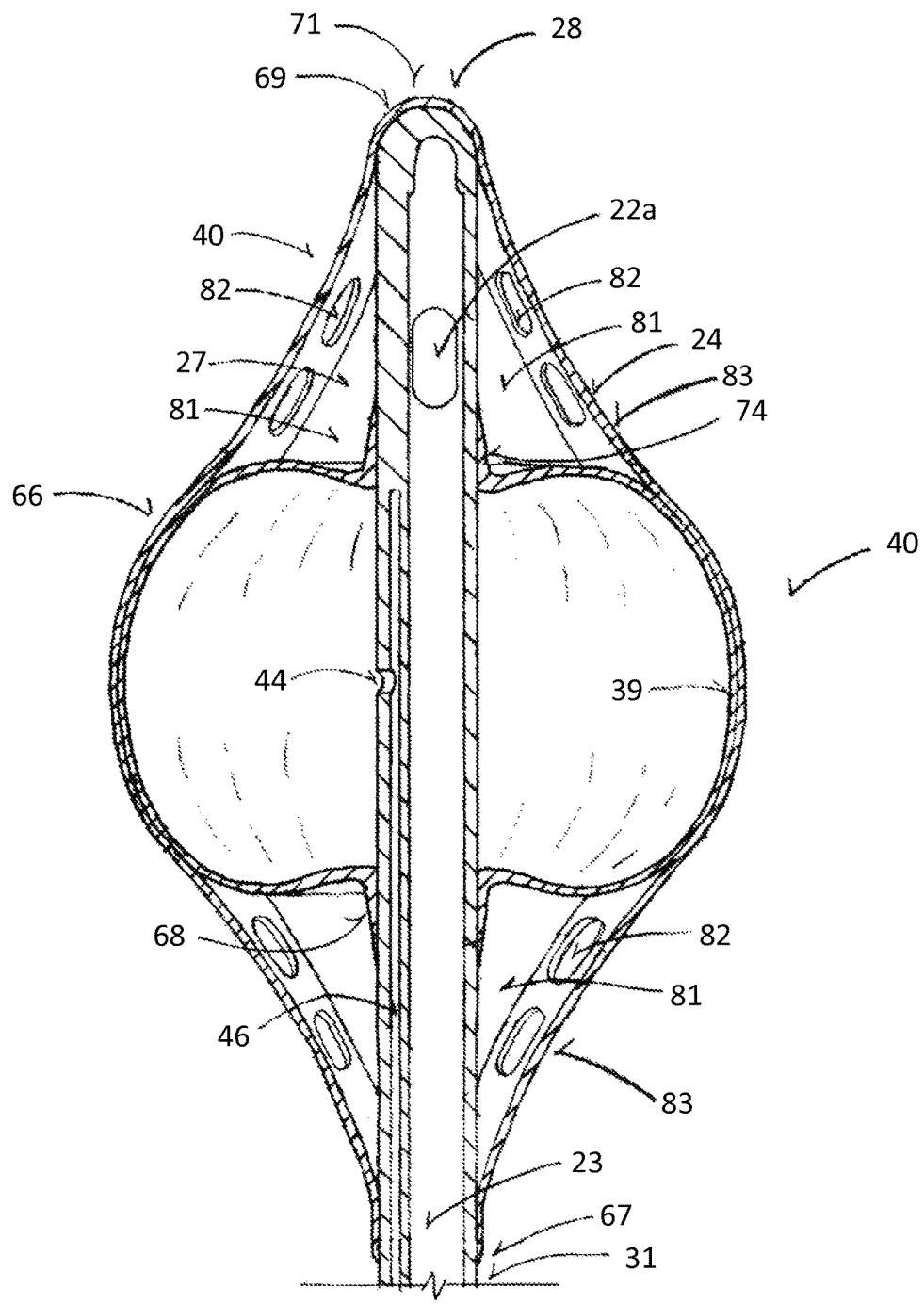
FIG. 19 depicts an enlarged sectioned view of the distal portion of an embodiment of a FMID catheter in an expanded state having relatively larger membrane entry ports between membrane struts at both the proximal and distal ends of the retention element.
Figure 20:
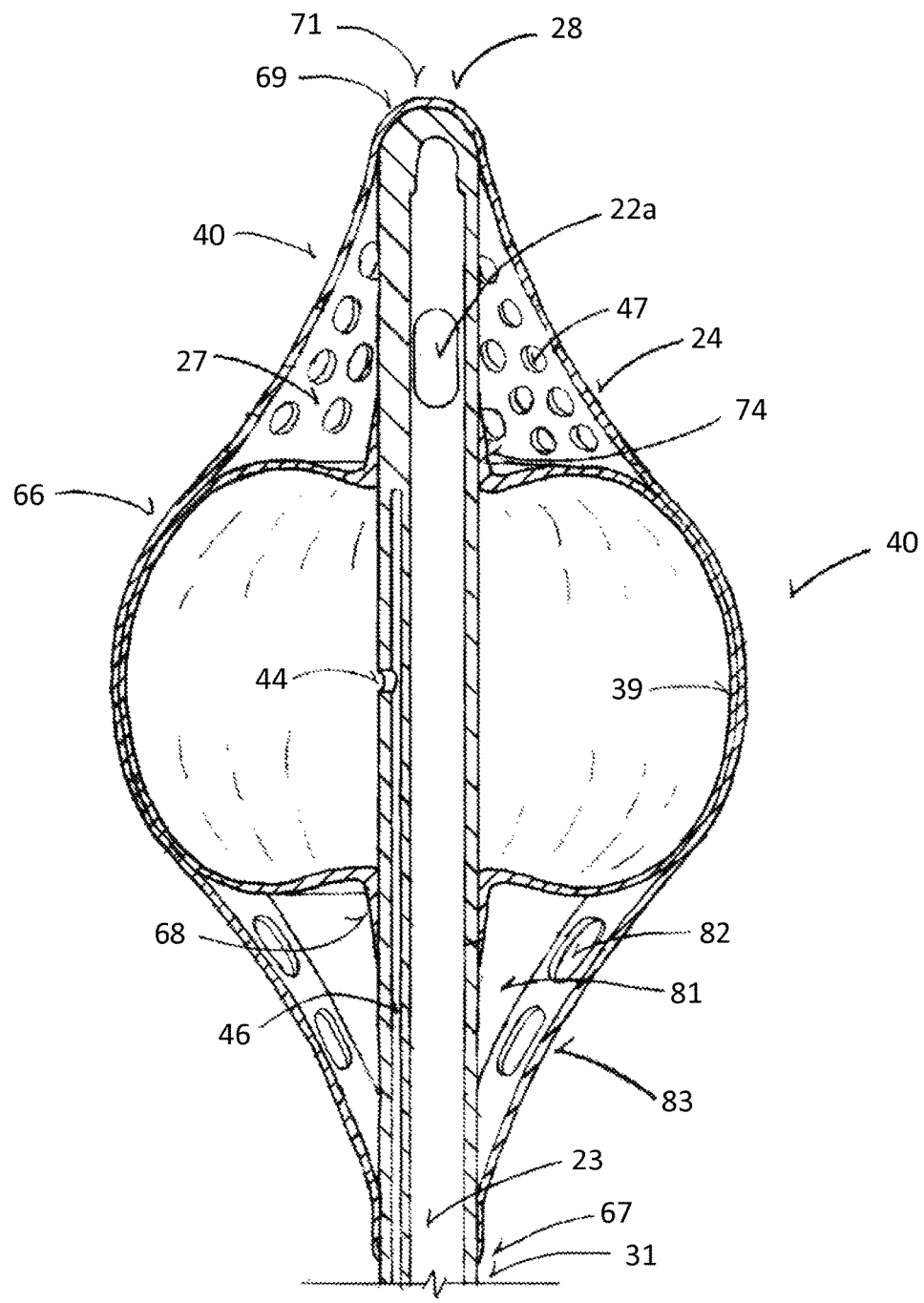
FIG. 20 depicts an enlarged sectioned view of the distal portion of an embodiment of a FMID catheter in an expanded state having relatively larger membrane entry ports between membrane struts at only the proximal end of the retention element.
Figure 21:
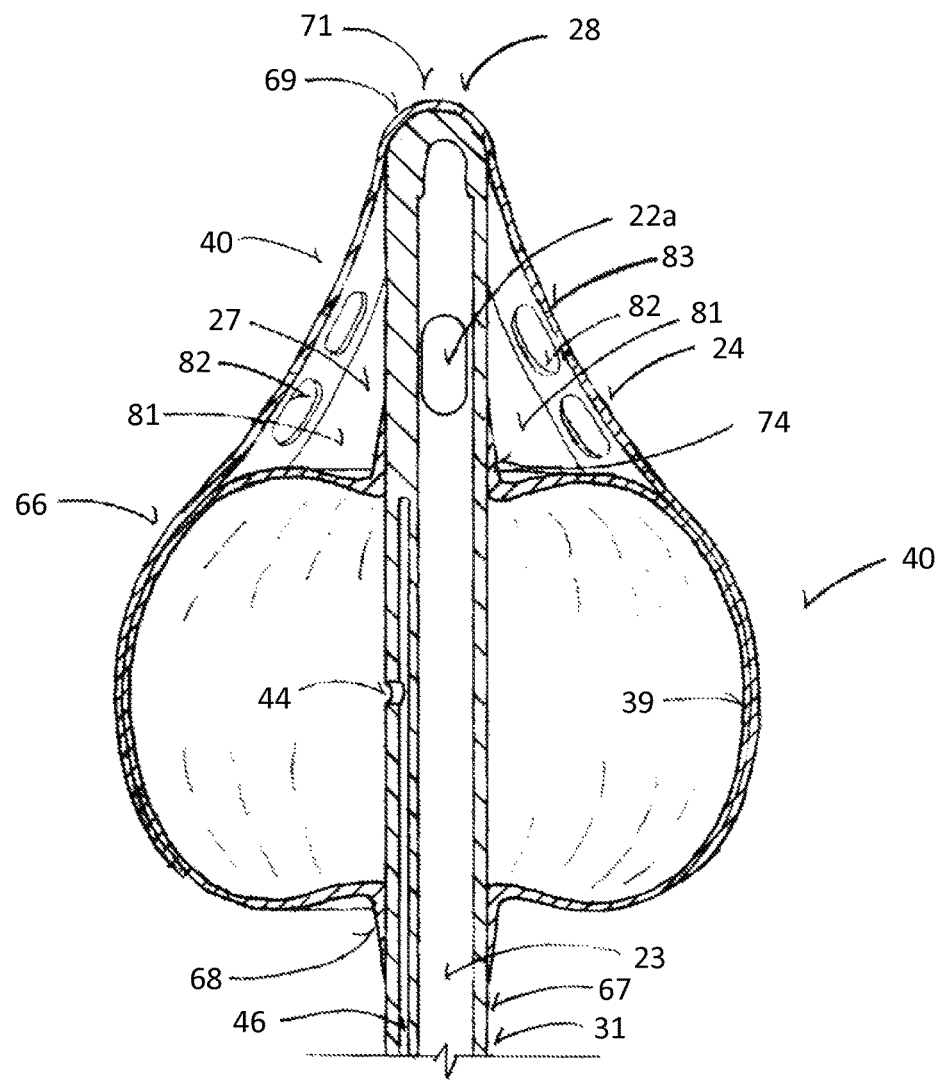
FIG. 21 depicts an enlarged sectioned view of the distal portion of an embodiment of a FMID catheter in an expanded state having relatively larger membrane entry ports between membrane struts at only the distal end of the retention element.

Now turning to FIGS. 19-21, which are depicting a pictorial view of still further embodiments of a FMID catheter 20 having one or more relatively larger membrane entry ports 81 disposed between membrane struts 83 in an expanded state. As can be appreciated in FIGS. 19-21, some embodiments may include a filter membrane 24 configured to encapsulate only a portion of the retention element 39 and/or only partially cover the retention element 39. FIG. 19 depicts an enlarged sectioned view of the distal portion of a FMID catheter 20 with a partially covering filter membrane 24. Here, the partially covering filter membrane 24 expands to reveal relatively larger membrane entry ports 81 between membrane struts 83 at the distal 74 and proximal ends 68 of the retention element 39. The membrane entry ports 81 open to the interstitial drainage cavities 27 (that exist once the retention element 39 is expanded and enlarge as the filter membrane 24 is pushed away from elongated cylindrical element 31) defined by the void at the distal 74 and proximal ends 68 of the retention element 39 between the elongated cylindrical element 31 and the filter membrane 24. The filter membrane 24 may include perforations to allow for further membrane entry ports 82 into the interstitial drainage cavities 27. The membrane entry ports 81 and/or 82 could be of any shape and any size with a cross-sectional area that is equal or larger than the drainage port(s) 22.

In some embodiments, as shown in FIG. 20, the filter membrane 24 encapsulates only the distal end 74 cavity 27 of the retention element 39 with a plurality of perforations 47 as previously described, and having relatively larger membrane entry ports 81 between membrane struts 83 at the proximal end 68 cavity 27. In still other embodiments, as shown in FIG. 21, the filter membrane has relatively larger membrane entry ports 81 between membrane struts 83 at the distal end 74 cavity 27 without an encapsulating membrane 24 portion, or with a proximal end 68 encapsulating membrane 24 portion (not shown).

Thus, the relatively larger membrane entry ports 81 between membrane struts 83 reduce the detrimental effects caused by the suction forces of the drainage ports 22 on the body cavity being drained, and reduce the risk of infection of the body cavity being drained by decreasing the residual volume of fluid retained in the body cavity being drained. Other features described above for the retention drainage catheters may also be incorporated into the embodiments having the relatively larger membrane entry ports 81 between membrane struts 83. As described above, internal interstitial drainage channels 26 may be created between the expanded wedges of a segmented retention element 39 and the filter membrane 24 in some embodiments so that the cavities 27 are in communication. Alternatively, the interstitial drainage channels 26 can be disposed on a segmented retention element 39 such that they (26) are not under the filter membrane 24 when in the expanded state. Also note that the proximal drainage port 22b is optional in this embodiment.

The invention further provides methods of manufacturing the FMID catheter 20 such as would be apparent to one of skill in the art given the disclosure and objectives of this disclosure. The FMID catheter 20 can be configured into any number of catheter designs comprising but not limited to, straight Foley, Coude' tip Foley, Council tip Foley, 3-way Foley, Whistle tip, spanning tandem balloon, Malecot catheters, subsumed tip, and any other catheter design presently existing or developed in the future. The FMID catheter 20 being of a material comprising at least one from a group of any biologically inert, biologically non-inert, naturally occurring, synthetic, non-biodegradable, biodegradable, and bioresorbable materials now known or later discovered in the future that are acceptable within the art for manufacturing catheter components, comprising but not limited to elastomeric materials, polymers, copolymers, metals and metal alloys. Exemplary materials are elastomeric, latex, and silicone. The retention element 39 and filter membrane 24 components are preferably made of an expandable silicone, latex rubber, silicone-based material, latex-based material, and/or combinations thereof. In some embodiments, especially where the filter membrane 24 possesses membrane properties, elastomeric material having micropores for filtering fluids and/or dissolved materials may be utilized. Thermo-sensitive materials, which change resiliency and or size at different temperatures, are contemplated to be within the scope of the disclosure. The filter membrane 24 and/or the retention element 39/64 may be affixed by any known method, including by adhesive, heat/chemical welding, mechanical fasteners, and/or combinations thereof. Preferably, a biocompatible latex or silicone adhesive is used.

The FMID catheter 20 can be coated or impregnated with therapeutic agents, such as but not limited to, antibiotics, antiseptics, blood clotting factors, growth factors, steroids, or any other materials and substances now known or later discovered in the future. The FMID catheter 20 can be coated or impregnated with fluorescent or radiopaque materials for radiological imaging. Applicants intend to encompass any structure presently existing or developed in the future that performs the same function.

The terms "comprising," "including," and "having," as used in the claims and specification herein, shall be considered as indicating an open group that may include other elements not specified. The terms "a," "an," and the singular forms of words shall be taken to include the plural form of the same words, such that the terms mean that one or more of something is provided. The term "one" or "single" may be used to indicate that one and only one of something is intended. Similarly, other specific integer values, such as "two," may be used when a specific number of things is intended. The terms "preferably," "preferred," "prefer," "optionally," "may," and similar terms are used to indicate that an item, condition or step being referred to is an optional (not required) feature of the invention.

The FMID catheter 20 and methods have been described with reference to various specific and preferred embodiments and techniques. However, it should be understood that many variations and modifications may be made while remaining within the spirit and scope of the invention. It will be apparent to one of ordinary skill in the art that methods, devices, device elements, materials, procedures and techniques other than those specifically described herein can be applied to the practice of the invention as broadly disclosed herein without resort to undue experimentation. All art-known functional equivalents of methods, devices, device elements, materials, procedures and techniques described herein are intended to be encompassed by this invention.

While the invention has been described with respect to a limited number of embodiments, those skilled in the art, having benefit of this disclosure, will appreciate that other embodiments can be devised which do not depart from the scope of the invention as disclosed herein. This invention is not to be limited by the embodiments disclosed, including any shown in the drawings or exemplified in the specification, which are given by way of example and not of limitation. Accordingly, the scope of the invention should be limited only by the attached claims.

We claim:

1. A drainage catheter comprising:
   a flexible elongated cylindrical element comprising a drainage port;
   a filter membrane comprising a membrane entry port disposed between membrane struts, wherein the membrane entry port has an individual cross sectional area that is equal to or larger than the cross sectional drainage area of the drainage port, wherein the drainage port is covered by the filter membrane; and
   a segmented expandable retention element, wherein the expandable retention element is disposed between the flexible elongated cylindrical element and the filter membrane.

2. The drainage catheter of claim 1, wherein the filter membrane is disposed over a distal portion of the flexible elongated cylindrical element having a proximal end and a distal end for inserting into a body cavity and an expandable retention element having a proximal end and a distal end.

3. The drainage catheter of claim 2, wherein the drainage port with the cross sectional drainage area is in fluid communication with a drainage lumen disposed within the flexible elongated cylindrical element.

4. The drainage catheter of claim 3, wherein the filter membrane is affixed to the flexible elongated cylindrical element near said distal end of the flexible elongated cylindrical element and near said proximal end of the expandable retention element.

5. The drainage catheter of claim 3, wherein the flexible elongated cylindrical element comprises two drainage ports, and wherein the filter membrane is affixed to the flexible elongated cylindrical element near said distal end of the flexible elongated cylindrical element and near said proximal end of the expandable retention element such that the two drainage ports are covered by the filter membrane.

6. The drainage catheter of claim 5, wherein the filter membrane comprises two membrane entry ports disposed between membrane struts and wherein one of the two membrane entry ports disposed between membrane struts is disposed at the proximal end of the expandable retention element and one of the two membrane entry ports disposed between membrane struts is disposed at the distal end of the expandable retention element.

7. The drainage catheter of claim 5, wherein the membrane entry port disposed between membrane struts is disposed at the proximal end of the expandable retention element and wherein the filter membrane at the distal end of the expandable retention element includes a plurality of perforations.

8. The drainage catheter of claim 3, wherein the membrane entry port disposed between membrane struts is disposed at the distal end of the expandable retention element.

9. The drainage catheter of claim 2, wherein the expandable retention element is a segmented expandable retention element.

10. The drainage catheter of claim 1, wherein the filter membrane includes a distal membrane affixing point that encapsulates the distal end of the flexible elongated cylindrical element.

11. A device comprising:
    a flexible elongated cylindrical element comprising a drainage port and having a distal portion with a distal end for inserting into a body cavity, a proximal end, and also having at least two lumina disposed within the flexible elongated cylindrical element;
    a filter membrane comprising a membrane entry port and affixed to the flexible elongated cylindrical element at the distal portion, wherein the membrane entry port has an individual cross sectional area that is equal to or larger than the cross sectional drainage area of the drainage port, wherein the drainage port is covered by the filter membrane; and
    segmented expandable retention element in fluid communication with at least a first lumen of said at least two lumina within the flexible elongated cylindrical element, wherein the expandable retention element is disposed between the flexible elongated cylindrical element and the filter membrane.

12. The device of claim 11, wherein the expandable retention element has a first non-expanded state in which the expandable retention element and the filter membrane lay substantially flat against the flexible elongated cylindrical element.

13. The device of claim 12, wherein the expandable retention element has a second expanded state in which the expandable retention element is filled with a fluid and the filter membrane expands with the filled expandable retention element.

14. The device of claim 13, wherein the drainage port is disposed on the flexible elongated cylindrical element and is in fluid communication with at least a second lumen of said at least two lumina within the flexible elongated cylindrical element for draining said body cavity.

15. The device of claim 14, wherein the filter membrane is affixed to the flexible elongated cylindrical element near said distal end and near the proximal end of the expandable retention element.

16. The device of claim 14, wherein the flexible elongated cylindrical element comprises two drainage ports and wherein the filter membrane is affixed to the flexible elongated cylindrical element near said distal end and near the proximal end of the expandable retention element such that the two drainage ports are covered by the filter membrane.

17. The device of claim 14, further comprising a distal internal interstitial drainage cavity and a proximal internal interstitial drainage cavity between the filter membrane and the flexible elongated cylindrical element.

18. The device of claim 17, wherein the retention element is comprised of a plurality of separate sub-retention element members.

19. The device of claim 16, wherein the flexible membrane comprises two membrane entry ports and wherein one of the two membrane entry ports disposed between membrane struts is disposed at the proximal end of the expandable retention element and one of the two membrane entry ports disposed between membrane struts is disposed at the distal end of the expandable retention element.

20. The device of claim 16, wherein the membrane entry port is disposed at the proximal end of the expandable retention element and wherein the filter membrane at the distal end of the expandable retention element includes a plurality of perforations.

21. The device of claim 20, wherein the membrane entry port has an individual cross sectional area that is larger than the individual cross sectional area of the plurality of perforations.

* * * * *